(12) United States Patent
Collier et al.

(10) Patent No.: US 9,730,898 B2
(45) Date of Patent: Aug. 15, 2017

(54) REVERSIBLE, ON-DEMAND GENERATION OF AQUEOUS TWO-PHASE MICRODROPLETS

(71) Applicants: UT-Battelle, LLC, Oak Ridge, TN (US); UNIVERSITY OF TENNESSEE RESEARCH FOUNDATION, Knoxville, TN (US)

(72) Inventors: Charles Patrick Collier, Oak Ridge, TN (US); Scott Thomas Retterer, Knoxville, TN (US); Jonathan Barton Boreyko, Knoxville, TN (US); Prachya Mruetusatorn, Knoxville, TN (US)

(73) Assignees: UT-BATTELLE, LLC, Oak Ridge, TN (US); UNIVERSITY OF TENNESSEE RESEARCH FOUNDATION, Knoxville, TN (US)

( * ) Notice: Subject to any disclaimer, the term of this patent is extended or adjusted under 35 U.S.C. 154(b) by 454 days.

(21) Appl. No.: 13/970,724

(22) Filed: Aug. 20, 2013

(65) Prior Publication Data
US 2015/0057371 A1 Feb. 26, 2015

(51) Int. Cl.
*B01L 3/00* (2006.01)
*A61K 9/50* (2006.01)
(Continued)

(52) U.S. Cl.
CPC .......... *A61K 9/5073* (2013.01); *A61K 9/5031* (2013.01); *A61K 9/5089* (2013.01);
(Continued)

(58) Field of Classification Search
CPC .................................................... A61K 9/5073
(Continued)

(56) References Cited

U.S. PATENT DOCUMENTS

2012/0322162 A1 12/2012 Collier et al.

OTHER PUBLICATIONS

Masahiro Yasukawa, Eiji Kamio, and Tsutomu Ono "Monodisperse Water-in-Water-in-Oil Emulsion Droplets" ChemPhysChem 2011, 12, 263-266.*

(Continued)

*Primary Examiner* — Christine T Mui
*Assistant Examiner* — Emily Berkeley
(74) *Attorney, Agent, or Firm* — Scully Scott Murphy & Presser

(57) ABSTRACT

The present invention provides methods of on-demand, reversible generation of aqueous two-phase microdroplets core-shell microbeads, microparticle preparations comprising the core-shell microbeads, and drug delivery formulation comprising the microparticle preparations. Because these aqueous microdroplets have volumes comparable to those of cells, they provide an approach to mimicking the dynamic microcompartmentation of biomaterial that naturally occurs within the cytoplasm of cells. Hence, the present methods generate femtoliter aqueous two-phase droplets within a microfluidic oil channel using gated pressure pulses to generate individual, stationary two-phase microdroplets with a well-defined time zero for carrying out controlled and sequential phase transformations over time. Reversible phase transitions between single-phase, two-phase, and core-shell microbead states are obtained via evaporation-induced dehydration and water rehydration.

18 Claims, 14 Drawing Sheets

(51) Int. Cl.
  *B01J 19/00* (2006.01)
  *G01N 1/34* (2006.01)
(52) U.S. Cl.
  CPC ...... *B01J 19/0093* (2013.01); *B01L 3/502784* (2013.01); *B01L 2200/0673* (2013.01); *B01L 2400/0406* (2013.01); *G01N 1/34* (2013.01)
(58) Field of Classification Search
  USPC .......................................................... 436/180
  See application file for complete search history.

(56) References Cited

OTHER PUBLICATIONS

Seung-Yong Jung, Scott T. Retterera and C. Patrick Collier "Interfacial tension controlled fusion of individual femtolitre droplets and triggering of confined chemical reactions on demand" Lab Chip, 2010, 10, 3373-3376.*
Supplementary Material (ESI) for Lab on a Chip "Interfacial tension controlled fusion of individual f emtolitre droplets and triggering of confined chemical reactions on demand" 2011.*
Sabina Santesson, Irene Barinaga-Rementeria Ramirez, Peter Viberg, Bengt Jergil, and Steffan Nilsson "Affinity Two-Phase Partitioning in Acoustically Levitated Drops" Anal. Chem. 2004, 76, 303-308.*
M. Scott Long, Ann-Sofie Cans, and Christine D. Keating "Budding and Asymmetric Protein Microcompartmentation in Giant Vesicles Containing Two Aqueous Phases" J. Am. Chem. Soc. 2008, 130, 756-762.*
Kalpana Vijayakumar, Shelly Gulati, Andrew J. deMello and Joshua B. Edel "Rapid cell extraction in aqueous two-phase microdroplet systems" Chem. Sci., 2010, 1, 447-452.*
Boreyko, J. et al., Self-Propelled Dropwise Condensate on Superhydrophobic Surfaces, Physical Review Letters, (Oct. 2009), vol. 103, pp. 184501-1-184501-4.
Dominak, L.M. et al., Microcompartmentation in Artificial Cells: pH-Induced Conformational Changes Alter Protein Localization, Langmuir, (2010), vol. 26, No. 8, pp. 5697-5705.
Dominak, L.M. et al., Polymer Encapsulation within Giant Lipid Vesicles, Langmuir, (2007), vol. 23, pp. 7148-7154.
Fiddes, L.K. et al., Flow of microgel capsules through topographically patterned microchannels, Lab Chip, (2007), vol. 7, pp. 863-867.
Frampton, J.P. et al., Precisely targeted delivery of cells and biomolecules within microchannels using aqueous two-phase systems, Biomed Microdevices, (2011), vol. 13, pp. 1043-1051.
Hahn, T. et al., Size-dependent detachment of DNA molecules from liquid-liquid interfaces, Soft Matter, (2011), vol. 7, pp. 6320-6326.
Helfrich, M.R. et al., Aqueous Phase Separation in Giant Vesicles, J. Am. Chem. Soc., (2002), vol. 124, pp. 13374-13375.
Jung, S. et al., Interfacial tension controlled fusion of individual femtolitre droplets and triggering of confined chemical reactions on demand, Lab Chip, (2010), vol. 10, pp. 3373-3376.
Andes-Koback, M. et al., Complete Budding and Asymmetric Division of Primitive Model Cells to Produce Daughter Vesicles with Different Interior and Membrane Compositions, J. Am. Chem. Soc., (2011), vol. 133, pp. 9545-9555.
Lai, D. et al., Rounded multi-level microchannels with orifices made in one exposure enable aqueous two-phase system droplet microfluidics, Lab Chip, (2011), vol. 11, pp. 3551-3554.
Lee, S. et al., Tunable spatial heterogeneity in structure and composition within acqueous microfluidic droplets, Biomicrofluidics, (2012), vol. 6, pp. 022005-1-022005-8.
Li, Y. et al., Transition from Complete to Partial Wetting within Membrane Compartments, J. Am. Chem. Soc., (2008), vol. 130, pp. 12252-12253.
Li, Y. et al., Membrane nanotubes induced by aqueous phase separation and stabilized by spontaneous curvature, PNAS, (Mar. 22, 2011), vol. 108, No. 12, pp. 4731-4736.
Li, Y. et al., Wetting-Induced Budding of Vesicles in Contact with Several Aqueous Phases, The Journal of Physical Chemistry, (2012), vol. 116, pp. 1819-1823.
Long, M.S. et al., Dynamic microcompartmentation in synthetic cells, PNAS, (Apr. 26, 2005), vol. 102, No. 17, pp. 5920-5925.
Long, M.S. et al., Budding and Asymmetric Protein Microcompartmentation in Giant Vesicles Containg Two Aqueous Phases, J. Am. Chem. Soc., (2008), vol. 130, 756-762.
Ma, S. et al., Fabrication of Microgel Particles with Complex Shape via Selective Polymerization of Aqueous Two-Phase Systems, small, (2012), vol. 8, No. 15, pp. 2356-2360.
Matosevic, S. et al., Stepwise Synthesis of Giant Unilamellar Vesicles on a Microfluidic Assembly Line, J. Am. Chem. Soc. (2011), vol. 133, pp. 2798-2800.
Meagher, R.J. et al., Rapid, continuous purification of proteins in a microfluidic device using genetically-engineered partition tags, Lab Chip, (2008), vol. 8, pp. 527-532.
Munchow, G. et al., Electrophoretic partitioning of proteins in two-phase microflows, Lab Chip, (2007), vol. 7, pp. 98-102.
Nam, K. et al., Continuous-Flow Fractionation of Animal Cells in Microfluidic Device Using Aqueous Two-Phase Extraction, Biomedical Microdevices, (2005), vol. 7, No. 3, pp. 189-195.
Santesson, S. et al., Affinity Two-Phase Partitioning in Acoustically Levitated Drops, Anal. Chem., (2004), vol. 76, pp. 303-308.
Sauret, A. et al., Forced generation of simple and double emulsions in all-aqueous systems, Applied Physics Letters, (2012), vol. 100, pp. 154106-1-154106-4.
Shum, H. et al., Microfluidic fabrication of water-in-water (w/w)jets and emulsions, Biomicrofluidics, (2012), vol. 6, pp. 012808-1-012808-9.
Song, Y. et al., Monodisperse w/w/w Double Emulsion Induced by Phase Separation, Langmuir, (2012), vol. 28, pp. 12054-12059.
Soohoo, J.R. et al., Microfluidic aqueous two phase system for leukocyte concentration from whole blood, Biomed Microdevices, (2009), vol. 11, pp. 323-329.
Soo Song, Y. et al., Microextraction in a tetrabutylammonium bromide/ammonium sulfate aqueous two-phase system and electrohydrodynamic generation of a micro-droplet, Journal of Chromatography A, (2007), vol. 1162, pp. 180-186.
Tsukamoto, M. et al., Cell separation by an aqueous two-phase system in a microfluidic device, Analyst, (2009), vol. 134, pp. 1994-1998.
Tumarkin, E. et al., Microfluidic generation of microgels from synthetic and natural polymers, Chem. Soc. Rev., (2009), vol. 38, pp. 2161-2168.
Vijayakumar, K. et al., Rapid cell extraction in aqueous two-phase microdroplet systems, Chem. Sci., (2010), vol. 1, pp. 447-452.
Yamada, M. et al., Continuous Cell Partitioning Using an Aqueous Two-Phase Flow System in Microfluidic Devices, Biotechnology and Bioengineering, (Nov. 20, 2004), vol. 88, No. 4, pp. 489-494.
Ziemecka, I. et al., Monodisperse hydrogel microspheres by forced droplet formation in aqueous two-phase systems, Lab Chip, (2011), vol. 11, pp. 620-624.

\* cited by examiner

REVERSIBLE, ON-DEMAND GENERATION OF AQUEOUS TWO-PHASE MICRODROPLETS

This invention was made with government support under Prime Contract No. DE-AC05-00OR22725 awarded by the U.S. Department of Energy. The government has certain rights in the invention.

FIELD OF THE INVENTION

Aqueous two-phase systems contained within microdroplets enable a bottom-up approach to mimicking the dynamic microcompartmentation of biomaterial that naturally occurs within the cytoplasm of cells. The present invention relates to the generation of femtoliter aqueous two-phase droplets within a microfluidic oil channel using gated pressure pulses to generate individual, stationary two-phase microdroplets with a well-defined time zero for carrying out controlled and sequential phase transformations over time. Reversible phase transitions between single-phase, two-phase, and core-shell microbead states were obtained via evaporation-induced dehydration and water rehydration. This system enables the controlled isolation and reversible transformation of a single microdroplet and is useful for dynamic microcompartmentation and affinity partitioning.

BACKGROUND OF THE INVENTION

Aqueous solutions containing two different polymers can be immiscible when mixed together above critical concentrations. The resulting interface of aqueous two-phase systems (ATPS) exhibits a remarkably low surface tension (~1-100 $\mu N\ m^{-1}$), allowing for biomolecules to readily traverse between the phases without denaturation [Ryden et al. (1971) J. Colloid Interface Sci. 37:219-222; Liu et al. (2012) Langmuir 28:3831-3839]. For this reason, ATPS are of great interest for the partitioning and self-assembly of biomaterials by exploiting their affinity for one of the polymer phases [Alberts son (1986) "Partitioning of Cell Particles and Macromolecules" Wiley, N.Y.; Walter et al. (1991) Anal. Biochem. 197:1-18; Azevedo et al. (2009) Trends Biotechnol. 27:240-247]. Over the past decade various microfluidic devices have used polymer solutions such as poly(ethylene glycol) (PEG) and dextran to generate aqueous two-phase flows capable of partitioning cells [Yamada et al. (2004) Biotechnol. Bioeng. 88:489-494; Nam et al. (2005) Biomed. Microdevices 7:189-195; Tsukamoto et al. (2009) Analyst 134:1994-1998; SooHoo et al. (2009) Biomed. Microdevices 11:323-329; Frampton et al. (2011) Biomed. Microdevices 13:1043-1051], proteins [Munchow et al. (2007) Lab Chip 7:98-102; Meagher et al. (2008) Lab Chip 8:527-532], and DNA [Hahn et al. (2011) Soft Matter 7:6320-6326].

Recently there has been much interest in containing ATPS within droplets to mimic the differences in local composition within the cytoplasm of cells, known as microcompartmentation [Munchow 2007]. This interest has been motivated by evidence that aqueous phase-separation is an important mechanism for cellular microcompartmentation, [Walter et al. (1995) FEBS Lett. 361:135-139; Ge et al. (2009) J. Am. Chem. Soc. 131:9094-9099], including the observation that P granules in germ cells are liquid droplets, and therefore some intracellular compartments are entirely aqueous in composition [Brangwynne et al. (2009) Science 324:1729-1732]. An acoustically levitated aqueous two-phase droplet was used to demonstrate the affinity partitioning of biotinylated liposomes [Santesson et al. (2004) Anal. Chem. 76:303-308]; however the millimetric droplet size is incommensurate with cellular length scales. Synthetic cells have been developed by encapsulating ATPS inside of spherical lipid bilayer membranes. [Helfrich, et al. (2002) J. Am. Chem. Soc. 124:13374-13375] In these systems, proteins could be preferentially sorted into the PEG or dextran-rich phase via affinity partitioning [Long et al. (2005) Proc. Natl. Acad. Sci. U.S.A. 102:5920-5925] or by tuning the pH. [Dominak et al. (2010) Langmuir 26:5697-5705]. However, this encapsulation method, while effective, results in a wide variety of vesicle sizes and morphologies, such as multilamellar vesicles and vesicles where each phase is additionally encapsulated by separate lipid bilayers [Long 2005]. The concentrations of the encapsulated polymers and molecules also tend to vary between vesicles [Dominak et al. (2007) Langmuir 23:7148-7154], and during osmotic deflation the lipid bilayer is wetted by both phases [Li et al. (2008) J. Am. Chem. Soc. 130:12252-12253] and becomes unstable, resulting in vesicle budding [Long et al. (2008) J. Am. Chem. Soc. 130:756-762; Li et al. (2011) Proc. Natl. Acad. Sci. U.S.A. 108:4731-4736; Li et al. (2012) Phys. Chem. B 116:1819-1823] and fission [Andes-Koback et al. (2011) J. Am. Chem. Soc. 133:9545-9555].

Formation of ATPS inside of vesicles has not yet been demonstrated in a microfluidic device, although a recent work showed successful encapsulation of a single phase of dextran inside monodisperse lipid membranes within a micro-channel [Matosevic et al. (2011) J. Am. Chem. Soc 133:2798-2800]. Without resorting to lipid membranes [Matosevic (2011)] or levitation [Santesson 2004], a double emulsion is required to contain an ATPS within a microdroplet. Obtaining even a single emulsion (e.g., a dextran drop inside a continuous PEG phase) within a microfluidic ATPS is not trivial, however, as the low surface tension makes it difficult to break up streams or jets into individual microdroplets. Currently, single emulsion (w/w) microfluidic ATPS have been achieved by electrically [Song et al. (2007) J. Chromatogr., A, 1162:180-186; and Ziemecka et al. (2011a) Lab Chip 11:620-624] or mechanically [Shum et al. (2012) Biomicrofluidics 6:012808; Sauret et al. (2012) Appl. Phys. Lett. 100:154106] perturbing a jet, or by fabricating rounded multi-leveled microchannels to induce flow instabilities [Lai et al. (2011) Lab Chip 11:3551-3554].

Very recently, all-aqueous (w/w/w) double emulsions were obtained in a microchannel using electrical [Ziemecka (2011b) Soft Matter 7:9878-9880] and mechanical pulsations [Sauret (2012); Song et al. (2012) Langmuir 28:12054-12059]. Interestingly, both PEG-in-dextran-in-PEG and dextran-in-PEG-in-dextran systems were possible, although these types of all-aqueous double emulsions are inherently unstable and break down to their phase separated states within seconds [Lai (2011)] or minutes [Ziemecka (2011b)]. A dextran-in-PEG-in-oil (w/w/o) ATPS, on the other hand, is both stable and conducive to droplet pinch-off due to the large surface tension of the water/oil interface. Previously, aqueous two-phase droplets in an oil microchannel have been obtained using a T-junction [Vijayakumar et al. (2010) Chem. Sci. 1:447-452; Lee et al. (2012) Biomicrofluidics, 6, 022005] or flow-focusing cross junctions [Ma et al. (2012) Small, 8:2356-2360].

The present invention makes possible generation of femtoliter-volume, aqueous two-phase droplets in an oil microchannel. In contrast to other reports of aqueous two-phase microdroplets, which rely on continuous flows/jets and high-frequency droplet formation, [Sauret (2012); Ziemecka (2011b); Song (2012); Vijayakumar (2010); Lee (2012); Ma (2012)] the devices herein and methods of the invention exploit the interfacial tension between the oil and aqueous phases to generate ultrasmall two-phase droplets with a well-defined time zero and without crossflow in the oil phase. This allows individual droplets to be monitored for extended times and to carry out programmed sequential phase transitions. Due to the large surface area to volume ratio of the microdroplets, single-phase droplets with initially low polymer concentrations transition to two-phase droplets during evaporation, and subsequently transition further to core-shell microbeads. These phase transitions are fully reversible by rehydration via fusion with an additional droplet of pure water. The controlled generation and interconversion of single-phase and two-phase microdroplets allows dynamic microcompartmentation and affinity partitioning, and the reversible creation of core-shell microbeads allows controlled delivery of encapsulated biomaterials.

SUMMARY OF THE INVENTION

The present invention relates to reversible, on-demand generation of aqueous two-phase microdroplets using a microfluidic device. The instant invention thus provides a method for forming an aqueous two-phase microdroplet which comprises (a) generating a first aqueous microdroplet by applying a pressure pulse through a first side microchannel of a microfluidic device, wherein the microfluidic device comprises a central microchannel having a communication junction with a first side microchannel and, approximately opposing said first side microchannel, having a communication junction with a second side microchannel, the central microchannel containing an aqueous-immiscible phase, the first side microchannel containing a first aqueous phase and the second microchannel containing a second aqueous phase, wherein said the first and second aqueous phases are capable of phase separation, and wherein the height and width of the side microchannels at the communication junctions are sufficiently smaller than the height and width of the central microchannel so that a pressure pulse applied through a side microchannel creates an interfacial tension induced force sufficient to form a microdroplet having a diameter of from about 0.2 µm to about 100 µm; (b) generating a second aqueous microdroplet by applying a pressure pulse through the second side microchannel in the microfluidic device; and (c) allowing the first and second microdroplets to coalesce to form a two-phase microdroplet.

In another embodiment, the method for forming an aqueous two-phase microdroplet comprises (a) generating an aqueous microdroplet in a microfluidic device by applying a pressure pulse through a side microchannel containing a first aqueous phase, wherein the microfluidic device comprises a central microchannel containing an aqueous-immiscible phase having a communication junction with the side microchannel, wherein the height and width of the side microchannel at the communication junction is sufficiently smaller than the height and width of the central microchannel so that the pressure pulse creates an interfacial tension induced force sufficient to form a microdroplet having a diameter of from about 0.2 µm to about 100 µm, and wherein the aqueous phase comprises a single phase mixture of two aqueous solutions capable of phase separation; and (b) allowing passive water evaporation from the microdroplet to occur until a two-phase microdroplet is formed.

In some embodiments of the foregoing methods, the aqueous-immiscible phase can be an oil or mixture of oils. In other embodiments, each of the pressure pulses creates an interfacial tension induced force sufficient to form a microdroplet having a diameter of from about 1 µm to about 20 µm and/or from about 5 µm to about 15 µm. In some embodiments, each of the height and width of the side microchannel independently ranges from about 0.2 µm to about 3 µm and each of the height and width of the central microchannel independently ranges from about 10 µm to about 40 µm. In other embodiments, each of the height and width of the side microchannels independently ranges from approximately 0.1 µm to about 5 µm. In yet other embodiments, each of the height and width of the central microchannel independently ranges from about 1 µm to about to about 300 µm.

For some embodiments of the method in which two aqueous microdroplets are actuated, the first aqueous phase can be an aqueous solution comprising a first polymer and the second aqueous phase can be an aqueous solution comprising a second polymer, provided that the second polymer is different from the first polymer, and the polymers are present in concentrations sufficiently above the binodal curve for that polymer mixture to form a two phase system upon coalescence of the first and second microdroplets. For example, one pair of such polymers is polyethylene glycol (PEG) and dextran. Further, in other embodiments of this method, either or both of the first or second aqueous phases comprise one or more compounds or biomolecules capable of partitioning between the two aqueous phases. In some embodiments of this method, one of the first or second aqueous phases comprise one or more compounds or biomolecules incapable of partitioning between the first and second aqueous phases, whereas the other of the two second aqueous phases comprise one or more compounds or biomolecules capable of partitioning between the two aqueous phases. Finally, one or both of the two aqueous phases can comprise one or more compounds or biomolecules incapable of partitioning between the two aqueous phases.

For some embodiments of the method using a single aqueous microdroplet with a solution that is capable of phase separation upon passive water evaporation, the aqueous phase comprises a mixture of different first and second polymers at concentrations sufficiently below the binodal curve (for that mixture) to remain in a single phase prior to microdroplet formation but after microdroplet formation can separate into a two phase system during passive water evaporation. In such embodiments, the aqueous phase comprises one or more compounds or biomolecules capable of partitioning between the phases of said two phase microdroplet, or one or more compounds or biomolecules incapable of partitioning between the phases of said two phase microdroplet.

Another aspect of the invention relates to a method of forming a core-shell microbead which comprises (a) preparing an aqueous two-phase microdroplet in accordance with the invention and (b) allowing passive water evaporation to occur until the microdroplet remains at a constant size, thereby forming a core-shell microbead.

Yet another aspect of the present invention is directed to a method of producing reversible phase transitions in a microdroplet by (a) generating an aqueous two-phase microdroplet from a single phase mixture of two aqueous solutions capable of phase separation in accordance with the invention; (b) allowing passive water evaporation from the microdroplet to occur until a two-phase microdroplet or a core shell microbead is formed; and (c) generating a second aqueous microdroplet in accordance with the invention by applying a pressure pulse through a second side microchannel containing a second aqueous phase capable of coalescing with said two-phase microdroplet or said microbead and inducing a phase transition. The second aqueous phase can be, but is not necessarily, water. This method (steps b and c) can be repeated one or more times to produce one or more further phase transitions.

A yet further aspect of the invention is directed to making microparticle preparations by (a) applying multiple pressure pulses to generate aqueous two-phase microdroplets in accordance with a method of the invention; (b) applying a backing pressure to the central microchannel to move each microdroplet into a collection reservoir and allowing passive water evaporation to occur until each microdroplet remains at a constant size, thereby forming a core-shell microbead; and (c) recovering the core-shell microbeads from the collection reservoir to thereby produce a microparticle preparation. In this method, one or more of the aqueous solutions used in forming the microdroplets can comprise a drug (or any other biomolecule of interest). The invention further provides a drug delivery formulation prepared by this method in admixture with a pharmaceutically-acceptable carrier.

Still an additional aspect of the invention provides a method of forming a microdroplet interface bilayer (microDIB) by (a) generating a first aqueous microdroplet by applying a pressure pulse through a first side microchannel of a microfluidic device, wherein the microfluidic device comprises a central microchannel having a communication junction with a first side microchannel and, approximately opposing the first side microchannel, having a communication junction with a second side microchannel, the central microchannel containing an aqueous-immiscible, lipid-containing phase, the first side microchannel containing a first aqueous phase and the second microchannel containing a second aqueous phase, and wherein the height and width of the side microchannels at the communication junctions are sufficiently smaller than the height and width of the central microchannel so that a pressure pulse applied through a side microchannel creates an interfacial tension induced force sufficient to form a microdroplet having a diameter of from about 0.2 μm to about 100 μm; (b) generating a second aqueous microdroplet by applying a pressure pulse through a second side microchannel in the microfluidic device; and (c) allowing the first and second microdroplets to fuse thereby forming an interface bilayer between said microdroplets. The first and second aqueous phases can be the same or different for the formation of microDIBs. MicroDIBs can be used, for example, to study lipid or other biomolecule diffusion.

DETAILED DESCRIPTION OF THE INVENTION

Figure 1:
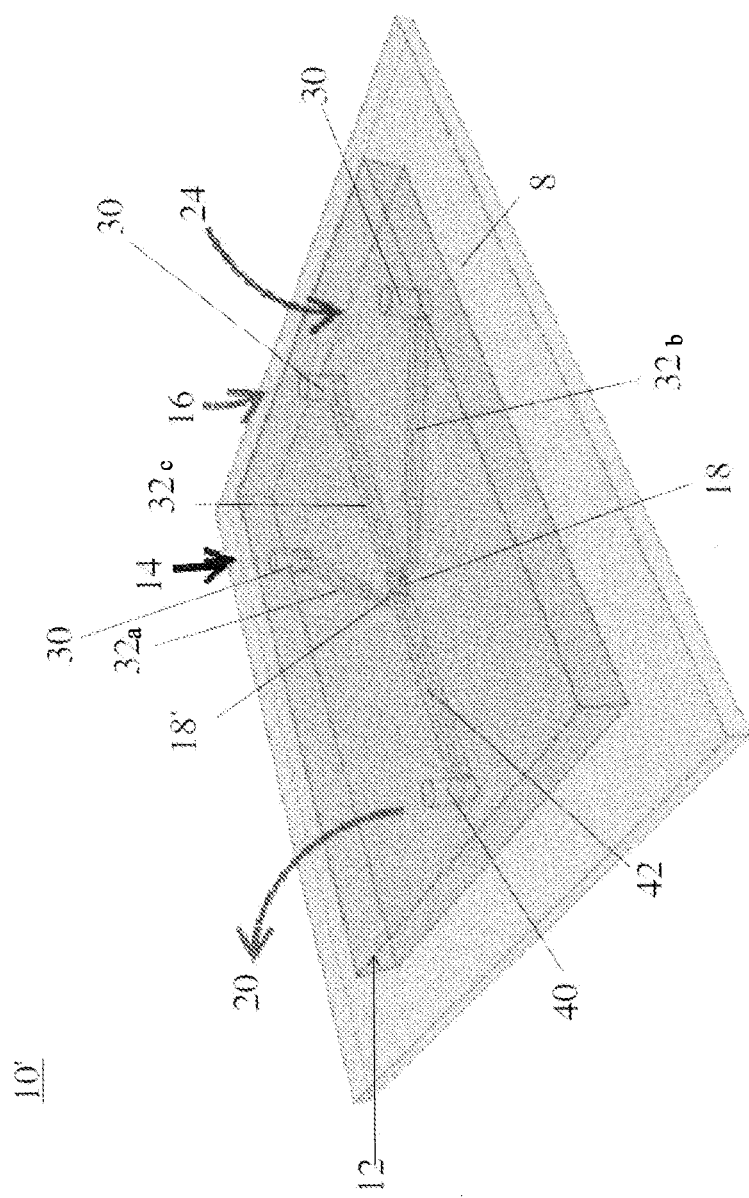
FIG. 1 is a schematice view of a microfluidic device that can be used in the present invention.

In accordance with the present invention, a method for forming an aqueous two-phase microdroplet comprises generating a first aqueous microdroplet by applying a pressure pulse through a first side microchannel of a microfluidic device. The microfluidic device comprises a central microchannel having a communication junction with a first side microchannel and, approximately opposing said first side microchannel, has a communication junction with a second side microchannel, with the central microchannel containing an aqueous-immiscible phase, the first side microchannel containing a first aqueous phase and the second microchannel containing a second aqueous phase, wherein the first and second aqueous phases are capable of phase separation. The height and width of the side microchannels at the communication junctions are sufficiently smaller than the height and width of the central microchannel so that a pressure pulse applied through a side microchannel creates an interfacial tension induced force sufficient to form a microdroplet having a diameter of from about 0.2 µm to about 100 µm. To form the aqueous two-phase microdroplet in accordance with the invention, generating a second aqueous microdroplet is generated by applying a pressure pulse through the second side microchannel in the microfluidic device; and the first and first and second microdroplets are allowed to coalesce to form the aqueous a two-phase microdroplet. The microdroplets can be actuated simultaneously or sequentially.

A general description of microfluidic devices for use in the invention, including materials, methods for making such devices and how to use the device, is provided in U.S. Patent Publication No. 2012/0322162 (the '162 publication). These microfluidic devices can be further adapted as needed for additional embodiments of the invention. For example, in some embodiments, the central microchannel can have multiple sets of opposing side microchannels. In other embodiments, the central microchannel can open into a collection reservoir (at the end opposite where pressure is applied, i.e., the flow through the central microchannel leads to the collection reservoir).

In some embodiments, the height and width of the side microchannel independently ranges from about 0.2 µm to about 3 µm and each of the height and width of the central microchannel independently ranges from about 10 µm to about 40 µm. In other embodiments, the height and width of the side microchannels independently range from approximately 0.1 µm to about 5 µm. In further embodiments, the height and width of the central microchannel independently range from about 1 µm to about to about 300 µm.

The '162 publication also describes how to apply pressure pulses to produce microdroplets on demand. For example, the microfluidic device can operate using pressure pulses that range up to 200 kPa. The pressure can be adjusted by utilizing a pressure regulator which is remote to the microfluidic device; no other equipment such as microinjectors, syringe pumps, actuators, etc. is needed. In some embodiments, a series of pressure pulses are used, and these can be performed simultaneously or sequentially from each side microchannel.

The term "interfacial tension induced force" denotes a force that depends on the interfacial tension and surface curvature of the oil-water interface of the aqueous droplet in the oil phase, or at a meniscus connecting the two phases inside a microchannel. In the context of forming a microdroplet on-demand with this method, the interfacial tension induced force is the driving force for spontaneously forming an individual droplet on-demand at a communication junction. This driving force arises from the abrupt change in channel dimension at the communication junction, which allows a nascent droplet room to assume a spherical shape, minimizing the interfacial tension and hence the surface energy of the droplet.

In accordance with the invention, microdroplets are generally spherical when formed (but can be deformed by flow) and have a diameter of about 0.2 µm to about 100 µm, and preferably from about 1 µm to about 20 µm, and more preferably from about 5 µm to about 15 µm. The microdroplets thus have sizes approximating organelles, bacteria, fungi, yeasts and eukaryotic cells.

An aqueous two-phase microdroplet is a single microdroplet which contains one or more smaller microdroplets within it. This single, or outer, microdroplet and the smaller microdroplets are each composed of different aqueous phases that are capable of stable phase separation under a given set of conditions (e.g., solute concentration, temperature, pH). While aqueous two-phase systems (ATPS) are well known, one can readily ascertain whether two aqueous solutions are immiscible (i.e., capable of phase separation), and under what conditions, by constructing a binodal curve using techniques known in the art such as turbidometric titration and the cloud-point method. For example, PEG solutions and dextran solutions are capable of phase separation at certain concentrations (see Examples).

The aqueous two-phase microdroplets that have diameters, after coalescence, ranging from about 5 to about 15 µm result in droplet volumes of V~100 fL, on the order of typical cellular volumes and one, three and five orders of magnitude smaller than previously reported aqueous two-phase droplets in oil channels [Ma (2012); Vijayakumar (2010); Lee (2012)] The small droplet size also promotes spontaneous mixing and phase separation, as the surface energy released upon coalescence becomes increasingly significant at micrometric length scales and results in dramatic droplet oscillations [Boreyko et al. (2009) Phys. Rev. Lett. 103:184501]. The complete mixing of two microdroplets upon coalescence was previously observed to occur in less than 1 ms [Jung et al. (2010a) Lab Chip 10:3373-3376] an order of magnitude faster than the diffusive mixing time scale and in good agreement with the near-instantaneous phase separation observed upon droplet fusion in accordance with the present invention. This contrasts previous reports, which typically required serpentine channels to achieve complete mixing and phase separation of larger aqueous two-phase droplets [Ma (2012); Vijayakumar (2010)]. Finally, while other devices required continuous flows to generate aqueous two-phase droplets [Sauret (2012); Ziemecka (2011b); Song (2012); Vijayakumar (2010); Lee (2012); Ma (2012)], the pressure pulses used here allow for the controlled formation of a single, stationary two-phase droplet with a well-defined time zero. This enables a controlled study of droplet behavior over extended times and can be used to observe dynamic phase transitions, molecular partitioning and microcompartmentation effects.

The aqueous phases used in the side microchannels include, water and aqueous solutions. Many polymer solutions are known to form ATPS but any pair of solutes (or combination of distinct solute pairs) that can generate an ATPS can be used in the side microchannels. Hence, in some embodiments, one side channel can contain a first aqueous phase while the other side channel contains a different aqueous phase, which upon actuation and coalescence of microdroplets in the microfluidic device, form an ATPS. In other embodiments, the first side channel contains a single aqueous phase mixture of two aqueous solutions capable of phase separation upon evaporation of sufficient water to raise solute concentrations above the binodal curve for the given mixture. Binodal curves for ATPS are generally known or can be readily determined by techniques known in the art.

Accordingly, polymers for use in embodiments of the invention are water soluble and can be synthetic or natural polymers. Water soluble polymers for use in pharmaceutical applications are well known [see, e.g., Kadajji et al. (2011) Polymers 3:1972-2009].

Examples of synthetic polymers, include but are not limited to, poly(ethylene glycol) (PEG); poly(ethylene oxide) (PEO) and other polyalkylene oxides, poly(propylene oxide) (PPO), polyvinyl pyrrolidone (PVP), polyvinyl pyrrolidone-vinyl acetate (PVP-VA) copolymer, polyvinyl alcohol (PVA), polyacrylic acid (PAA), poly(acrylic acid) (PAA) copolymers modified with block-copolymers of PEO and PPO, polyacrylamides, N-(2-hydroxypropyl) methacrylamide (HPMA), divinyl ether-maleic anhydride (DIVEMA), polyoxazoline, poly(2-alkyl-2-oxazolines), polyphosphoesters (PPE) like polyphosphates, polyphosphonates and polyphosphoramidates (PPAs), polyphosphazenes, polylactic acid (PLA), polyglycolic acid (PGA), polycaprolactone (PCL) and copolymers and mixtures thereof, poly(oxa) esters, polydioxanone (PDS), polypropylene fumarate, poly (ethyl glutamate-co-glutamic acid), poly(tert-butyloxy-carbonylmethyl glutamate), polycaprolactone co-butylacrylate, polyhydroxybutyrate (PHBT) and copolymers of polyhydroxybutyrate; poly(phosphazene), poly(phosphate ester), poly(amino acid), polydepsipeptides, maleic anhydride copolymers, polyiminocarbonate and the like.

Examples of natural polymers include, but are not limited to, xanthan gum, pectins, chitosan, chitosan derivatives, dextran, carrageenan, guar gum, cellulose, cellulose ethers, hyaluronic acid (HA), proteins (e.g., albumin), nucleic acids, starch or starch-based derivatives and the like.

To approximate conditions under which an ATPS can coexist for two aqueous solutions, one can construct a binodal for the system using cloud point titration or any other convenient technique.

In an embodiment of the invention with different aqueous phases in each side microchannels, the first aqueous phase is an aqueous solution comprising a first polymer and the second aqueous phase is an aqueous solution comprising a second, different polymer, with the polymers being present in concentrations sufficiently above the binodal curve for mixture to form a two phase system upon coalescence of said first and second microdroplets. An example of such solutions is a 4% PEG 35 kDa and 4% dextran 100 kDa; those of skill in the art can readily determine other solutions that have these phase separation abilities.

The aqueous-immiscible phase (also referred to herein as a water-immiscible liquid) for the central microchannel is a liquid and can be any fatty substance, especially oils, fatty alcohols, fatty acids, hydrocarbons, and the like which are capable of phase separation with an aqueous solution. In some embodiments, the water-immiscible liquid is an oil, or a mixture of oils, and can, optionally, contain other fatty substances such as lipids, fatty alcohols, fatty acids, waxes, and gums. Oils which may be used in the invention include mineral oil; vegetable oils such as jojoba oil, soybean oil, coconut oil, corn oil, cottonseed oil, olive oil, palm oil, peanut oil, rapeseed oil, safflower oil, sunflower oil, almond oil, cashew oil, hazelnut oil, walnut oil, citrus oil, carrot seed oil and castor oil; animal oils; synthetic oils; natural or synthetic essential oils; silicone oils; and fluorinated oils, such as perfluoropolyethers, e.g., FOMBLIN® or FLUORINERTS™ (3M). Hydrocarbons and halogenated hydrocarbons that can be used in the invention include, but are not limited to, hexadecane, octadecane, heptadecane, nonadecane, octadecanoic acid, and the like.

In another embodiment of the invention, the method for forming an aqueous two-phase microdroplet comprises (a) generating an aqueous microdroplet in a microfluidic device by applying a pressure pulse through a side microchannel containing a first aqueous phase which comprises a single phase mixture of two aqueous solutions capable of phase separation and (b) allowing passive water evaporation from the microdroplet to occur until a two-phase microdroplet is formed. For this embodiment, the microfluidic device comprises a central microchannel containing an aqueous-immiscible phase having a communication junction with said side microchannel, and the height and width of the side microchannel at the communication junction is sufficiently smaller than the height and width of the central microchannel so that the pressure pulse creates an interfacial tension induced force sufficient to form a microdroplet having a diameter of from about 0.2 μm to about 100 μm.

This method is directed to forming an aqueous two-phase microdroplet using passive water evaporation. The microfluidic device, how to make it and how to use it are as described above. Similarly, the aqueous phases and aqueous-immiscible phases are as described above. The first single phase mixture is sufficiently below the binodal curve so that phase separation does not occur in the microchannel but rather only begins once the droplet is actuated in to the central microchannel and evaporation begins. Using dry or water-soaked microfluidic devices, allows one to control the evaporation rate. In an embodiment, using a dry PDMS microdevice, the observed droplet shrinkage rate increased from ~10 μm² min⁻¹ to ~100 μm² min⁻¹ at 25° C. relative to a water-soaked PDMS device (see Examples). Microdroplets with large surface area to volume ratios such as those produced by the present inventions evaporate at this rate, and evaporation-induced phase transitions occur in a brief time span of only a few minutes.

Another aspect of the invention is directed to a method of forming a core-shell microbead. The method comprises preparing an aqueous two-phase microdroplet in accordance with the invention and allowing passive water evaporation to occur until the microdroplet remains at a constant size. Once the microdroplet retains a constant size, i.e., water evaporation is complete, a core-shell microbead has been formed. The inner core has the components of the smaller microdroplet(s) (or inner phase of the ATPS) and the outer shell has the components of the larger microdroplet or (the outer phase of the ATPS).

Passive water evaporation can occur in the presence or absence of a flow in the central microchannel (and this holds true whether forming an aqueous two phase microdroplet or a core-shell microbead). The flow in the central microchannel can be steady or pulsed. For example, in one embodiment, pressure pulses are applied through the side microchannels to actuate microdroplets, with the microdroplets having different immiscible aqueous phases and after the droplets coalesce, a pressure pulse is applied to the central microchannel to move the two-phase microdroplet towards a collection chamber. As the droplet moves toward the collection chamber, passive water evaporation occurs leading to the formation of a core-shell microbead. The alternation of side and central pressure pulses can repeated to form multiple core-shell microbead, which flow into the collection chamber. This method can also be formed using a steady flow in the central microchannel and repeated side pulses.

The core-shell microbeads of the present invention are distinct from hydrogel capsules [Fiddes et al. (2007) Lab Chip 7:863-867] and hydrogel microbeads [Ziemecka (2011a); Ma (2012)]. Hydrogels are formed by some type of polymerization [Tumarkin et al. (2009) Chem. Soc. Rev. 38:2161-2168] such as chemical cross-linking [Ziemecka (2011a)] and/or UV curing, [Ma (2012)] and remain stable even after prolonged immersion in water [Ziemecka (2011)]. The core-shell microbeads of the present invention, on the other hand, are the physical solidification of two aqueous solutions due to evaporation increasing the solute concentration to a critical level (e.g., a PEG solution and a dextran solution). As a result, these microbeads may be immediately transformed back into an aqueous phase when hydrated with water. While the core-shell microbeads of the invention can be observed for studying reversible phase transitions, applying a continuous flow can also generate a large number of core-shell microbeads for collection, when the central channel is long enough to enable the evaporation-induced phase transition from the aqueous state.

Each of the aqueous phases for any of the foregoing embodiments of the invention can independently further comprise additional compounds. The presence of such compounds can be used to study chemical and biological reactions, particularly to study enzyme kinetics, to form nanoparticles and microparticles, to study protein crystallization, for molecular synthesis, for molecular separation, to conduct single cell and organelle assays, for microemulsion synthesis, for molecular affinity partitioning, and for drug delivery. These aqueous compounds can be selected from aqueous organic compounds (i.e., organic compounds that are miscible in water), aqueous inorganic compounds, aqueous biomolecules, acids, bases, or their corresponding salts, or particulate matter suspended in aqueous solution, such as micro- or nanoparticles or beads.

When an aqueous organic compound is employed, the organic compound that can be employed must be miscible in water. Examples include, but are not limited to, halides, alcohols, ethers, carbonyls, aldehydes, ketones, esters, carboxylic acids, carboxylic acids chlorides, amides, amines, nitriles, nitros, sulfides, sulfoxides, and sulfones.

When an aqueous inorganic compound is employed, the inorganic compound must be miscible in water. Examples include, but are not limited to, metal acetates, metal halides, metal citrates, metal hydroxides, metal nitrates, metal nitrites, metal phosphates, and metal sulfates. The metal component can be any metallic element including, for example, alkali metals, alkaline earth metals, rare earth metals, transition metals, lanthanide metals, actinide metals and mixtures thereof. In one embodiment, aqueous solutions of $AgNO_3$ and $NaCl$ as dissolved salts are used as the aqueous inorganic compounds for the first and third phases. In such an embodiment, a fused monodisperse product droplet containing solid $AgCl$ precipitate can form.

When a biomolecule is employed, the biomolecule can include, but is not limited to, an amino acid, a protein, a peptide, phospholipids, sphingosines, fatty acids, ceramides, a sugar, an antigen, an antibody, an enzyme, serum, DNA, RNA, and any complexes formed from these compounds. The biomolecule can also include individual living cells or multiple living cells.

When an acid is employed, the acid includes any compound that dissociates in solution, releasing hydronium ions and lowering the solution pH (a proton donor). The acid can be an organic acid or a mineral acid. Illustrative examples of acids that can be employed include, but are not limited to, hydrochloric acid, nitric acid, phosphoric acid, sulfuric acid, hydrofluoric acid, hydrobromic acid, lactic acid, acetic acid, formic acid, citric acid, oxalic acid, and uric acid.

When a base is employed, the base includes any compound that can accept protons. Examples of suitable bases that can be employed include, but are not limited to, pyridine, methyl amine, imidazole, benzimidazole, histidine, phosphazene bases, potassium hydroxide, barium hydroxide, cesium hydroxide, sodium hydroxide, and lithium hydroxide.

For the study of enzyme kinetics, the course of a reaction can readily be followed using a fluorogenic or colorimetric assay. For example, one of the two aqueous phases can contain the enzyme under study and the other aqueous phase can contain a fluorogenic substrate for the enzyme, provided that one or both of the enzyme and its substrate can partition between the two aqueous phases. To initiate the assay, two aqueous microdroplets are actuated in accordance with the invention, the reaction initiates upon coalescence and the change in fluorescence is followed using the appropriate optical techniques. Methods of detecting changes in fluorescent and chromogenic substrates are well known in the art. The types of enzymes that can be studied include, but are not limited to, glycosidases, phosphatases, phosphate kinases, polymerases, nucleases, peptidases, proteases, oxidases, dealkylases, acetyltransferases, luciferases, dehydrogenase, lactamases and more.

In some embodiments, the aqueous phases used in the microchannels of the invention can contain none, one or more compounds that can partition between the two aqueous phases in any permutation. Additionally, in some embodiments, a first aqueous phase contains a compound that will not partition between the two phases, while the second aqueous phase contains a compound that does partition, thus allowing well controlled initiation of reactions, study of compartmentalization, molecular partitioning into defined phase and the like. Further, partitioning can be used in preparation of drug delivery formulations.

A yet further aspect of the invention is directed to making microparticle preparations by (a) applying multiple pressure pulses to generate aqueous two-phase microdroplets in accordance with a method of the invention; (b) applying a backing pressure to the central microchannel to move each microdroplet into a collection reservoir and allowing passive water evaporation to occur until each microdroplet remains at a constant size, thereby forming a core-shell microbead; and (c) recovering the core-shell microbeads from the collection reservoir to thereby produce a microparticle preparation. In this method, one or more of the aqueous solutions used in forming the microdroplets comprises a drug (or any other biomolecule of therapeutic interest).

The invention further provides a drug delivery formulation prepared by this method, that is a microparticle preparation of core-shell microbeads, in admixture with a pharmaceutically-acceptable carrier. Any drug, biological agent, or active ingredient compatible with the process of preparing the core-shell microbeads of the invention can be used. Doses of drugs and agents are known in the art and those of skill in the art can determine the amount of drug or agent desired for delivery, and calculate the amount of that should be loaded into core-shell microbeads. Further, the microparticle preparation can be coated with an enteric or other coating to prevent dissolution until the preparation reaches the desired physiological compartment (stomach, small intestines, etc.) for dissolution.

As used herein, "drugs" is used to include all types of therapeutic agents, whether small molecules or large molecules such as proteins, nucleic acids and the like. The drugs of the invention can be used alone or in combination.

Examples of non-steroidal anti-inflammatory agents include, but are not limited to, Acetominophen, aspirin, celecoxib, diclofenac, diflunisal, flurbiprofen, ibuprofen, indomethacin, ketoprofen, ketorolac, meclofenamate, meloxicam, methyl salicylate, nabumetone, naproxen, oxaprozin, piroxicam, sulindac, tolmetin and trolamine.

Examples of anesthetics include, but are not limited to, lidocaine, bupivacaine, mepivacaine and xylocaine. Local anesthetics have weak antibacterial properties and can play a dual role in the prevention of acute pain and infection.

Examples of antimicrobial drugs include, but are not limited to, aminoglycosides such as amikacin, gentamicin, kanamycin, neomycin, streptomycin, and tobramycin; antibiotics such as bacitracin, clindamycin, daptomycin, lincomycin, linezolid, metronid, polymyxin, rifaximin, vancomycin; cephalosporins such as cephazolin; macrolide antibiotics such as erythromycin, azithromycin and the like; β-lactam antibiotics such as penicillins; quinolones such as ciprofloxacin; sulfonamides such as sulfadiazine; tetracyclines such as minocycline and tetracycline; and other antibiotics such as rifampin, triclosan and chlorhexidine.

Still an additional aspect of the invention provides a method of forming a microdroplet interface bilayer (microDIB) by (a) generating a first aqueous microdroplet by applying a pressure pulse through a first side microchannel of a microfluidic device, wherein the microfluidic device comprises a central microchannel having a communication junction with a first side microchannel and, approximately opposing the first side microchannel, having a communication junction with a second side microchannel, the central microchannel containing an aqueous-immiscible, lipid-containing phase, the first side microchannel containing a first aqueous phase and the second microchannel containing a second aqueous phase, and wherein the height and width of the side microchannels at the communication junctions are sufficiently smaller than the height and width of the central microchannel so that a pressure pulse applied through a side microchannel creates an interfacial tension induced force sufficient to form a microdroplet having a diameter of from about 0.2 μm to about 100 μm; (b) generating a second aqueous microdroplet by applying a pressure pulse through a second side microchannel in the microfluidic device; and (c) allowing the first and second microdroplets to fuse thereby forming an interface bilayer between said microdroplets. The first and second aqueous phases can be the same or different for the formation of microDIBs. MicroDIBs can be used, for example, to study lipid or other biomolecule diffusion. The water immiscible-liquids and aqueous phases are as described above.

The generation of aqueous two-phase microdroplets in an oil microchannel has been achieved with requiring continuous flows or high-frequency droplet formation. Hence, the present system allows for the controlled production of an isolated two-phase microdroplet with no cross flow and a well-defined time zero. The large surface area to volume ratio of the femtoliter droplets can be exploited to passively obtain evaporation-induced phase transitions from single-phase to two-phase to core-shell microbead states. Reversible transitions from a core-shell microbead back to an aqueous two-phase or single-phase droplet are achieved by rehydration via fusion with an additional water droplet. The small femtoliter volume, static positioning, and reversible single-phase and two-phase states of the present aqueous two-phase microdroplets provides an ideal system for studies in the dynamic microcompartmentation and affinity partitioning of biomaterials. Furthermore, the reversible transitions between aqueous two-phase and solidified core-shell states provide for the controlled delivery of biomolecules and drugs.

The foregoing is considered as illustrative only of the principles of the invention.

Further, since numerous modifications and changes will readily occur to those skilled in the art, it is not desired to limit the invention to the exact construction and operation shown and described, and accordingly, all suitable modifications and equivalents may be resorted to, falling within the scope of the invention. All references patents, patent applications or other documents cited are herein incorporated by reference in their entirety.

Example 1

General Methods

An example of a microfluidic device is shown in FIG. 1. The microfluidic device 10' is composed of poly(dimethylsiloxane) (PDMS) 12 bonded to a PDMS-coated glass cover slip 8, and was fabricated as described [Jung (2010a); Jung et al. (2010b) Lab Chip 10:3373-3376]. To allow for droplet fusion, two opposing aqueous side-channels 32a and 32b (1 μm×1 μm, inputs 14 and 24, respectively, at junctions 18', 18, respectively) connect to either side of a central oil channel 32c of larger dimensions (14.6 μm wide×18 μm high, input 16). Entry ports for the channels are identified as 30, and exit port is designated as 40 (with exiting two-phase microdroplets designated as 20). The generation and fusion of droplets was obtained by applying pressure pulses to the side-channels; the abrupt change in channel height caused droplet formation to occur by virtue of shape-induced shear when the backing pressure exceeded the capillary pressure of the 1 μm×1 μm side-channels (124-131 kPa for pure water) [Jung (2010a]. PEG 35 kDa and dextran 100 kDa polymers (Sigma-Aldrich) were mixed with deionized water at varying concentrations and injected into the side-channels at entry ports 30. In some experiments, PEG-only and dextran-only solutions were injected in their respective side-channels, while in other experiments a solution containing both PEG and dextran was in one side-channel to allow for pure deionized water in the other. Purified soybean oil 42 was used as the continuous phase in the central channel 32c. The cross-flow in the oil channel was usually set to zero by balancing the slight hydrostatic pressure with a constant backing pressure; however, in select experiments a cross-flow was intentionally introduced by increasing the backing pressure. Bright field images were acquired using an inverted optical microscope (Eclipse TE300, Nikon Instruments) and a CCD camera (COOLSNAP™ HQ, Roper Scientific). For all experiments, the temperature was held to a constant 25° C. in a microscope cage incubator (Okolab H201).

Example 2

Generation of Single-Phase and Two-Phase Microdroplets

A bulk phase diagram for aqueous mixtures of PEG 35 kDa and dextran 100 kDa was constructed using cloud point titration (FIG. 2A, circular data points) [Liu (2012); Albertsson (1986)]. Dextran solutions were prepared in 10 mL test tubes with concentrations ranging from 0-20 wt %, and a stock solution of 10 or 20 wt % PEG was added dropwise until each solution became turbid upon shaking. The critical concentrations of PEG and dextran compose the binodal line, above which phase separation occurs and below which a single-phase mixture results.

Figure 2A:
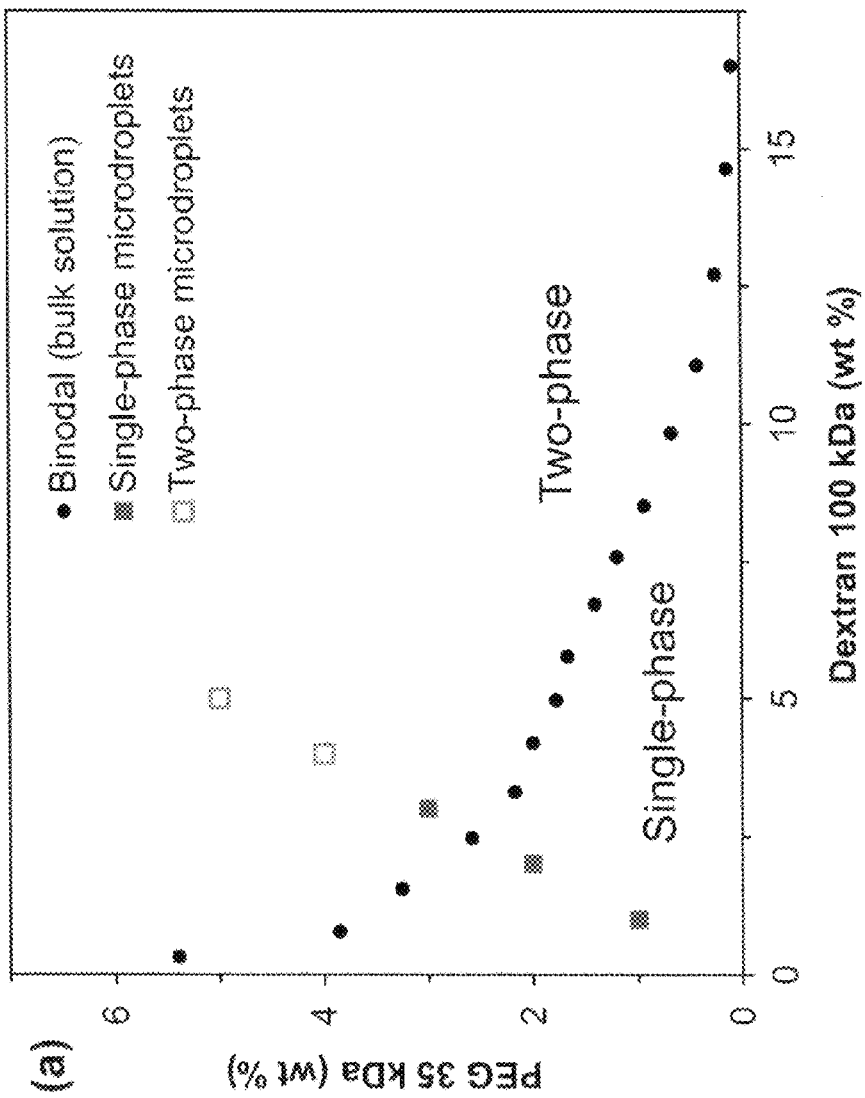
FIG. 2A provides a binodal bulk phase diagram for PEG 35 kDa and dextran 100 kDa at 25° C. generated by cloud point titration (circles). The additional points represent concentrations of PEG-only and dextran-only solutions in opposing microchannels for single-phase (solid squares) and two-phase (hollow squares) droplet formation in oil.
Figures 2B, 2C:
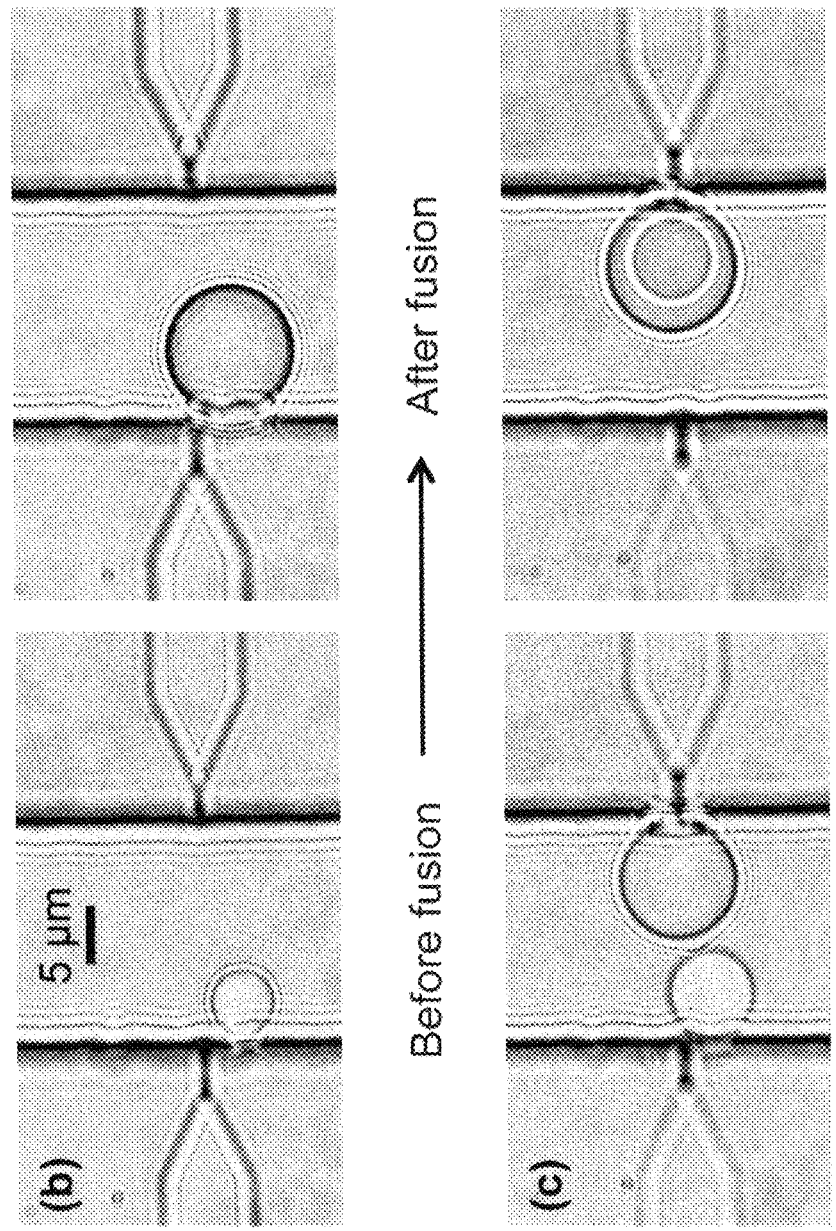
FIGS. 2B and C are video stills from before and after fusion of (b) a 3% dextran droplet (left channel) with a 3% PEG droplet (right channel) to form a single-phase droplet, and (c) a 4% dextran droplet (left channel) with a 4% PEG droplet (right channel) to form an aqueous two-phase droplet.

To obtain single-phase and two-phase droplets in the oil microchannel, and using the binodal curve as a guideline, separate PEG and dextran solutions were inserted into their respective side-channels, and their concentrations were varied from 1-5 wt % to cover both sides of the binodal. A pressure pulse was initialized in both side-channels to actuate a PEG drop and a dextran drop in the oil channel, and the resulting droplets' coalescence and phase behavior were observed and characterized. To minimize evaporation effects, the PDMS chip was saturated with deionized water by soaking it for at least 24 h prior to experiments. Initial polymer concentrations of 3% or smaller resulted in single-phase behavior upon coalescence (FIG. 2B), while phase separation with a dextran-rich droplet inside of a PEG-rich droplet occurred for concentrations of 4% and above (FIG. 2C). The inner drop was confirmed to always be the dextran-rich phase by combining a PEG drop and a dextran drop of differing volumes, in which case the volume of the inner phase always corresponded to that of the initial dextran drop.

The initial concentrations of PEG and dextran in the side-channels are not the same as their final concentrations in a merged drop with larger water volume. This is particularly true for non-partitioned, single-phase droplets, where the polymer concentrations will become roughly halved upon coalescence and explains why the 3% PEG and dextran concentrations used in the side-channels were single-phase upon droplet fusion, despite these initial concentrations being slightly above the binodal curve (FIG. 2A). Regardless, the overall phase behavior of fused droplets in the microchannel was well approximated by the bulk phase diagram, and for simplicity all polymer concentrations are referred to the well-controlled initial concentrations injected into the inlet reservoirs of the side-channels.

After coalescence, the diameter of a droplet typically ranged from 5 to 15 μm, depending on the amplitude and duration of the applied pressure pulses. This results in aqueous two-phase droplet volumes of V~100 fL, on the order of typical cellular volumes, and one, three and five orders of magnitude smaller than previously reported aqueous two-phase droplets in oil channels [Ma (2012); Vijayakumar (2010); Lee (2012)]. The small droplet size also promotes spontaneous mixing and phase separation, as the surface energy released upon coalescence becomes increasingly significant at micrometric length scales and results in dramatic droplet oscillations [Boreyko (2009)].

The complete mixing of two microdroplets upon coalescence was previously observed to occur in less than 1 ms [Jung (2010b)], an order of magnitude faster than the diffusive mixing time scale and in good agreement with the near-instantaneous phase separation observed upon droplet fusion. This contrasts to previous reports, which typically required serpentine channels to achieve complete mixing and phase separation of larger aqueous two-phase droplets [Vijayakumar (2010); Ma (2012)]. Finally, while other devices required continuous flows to generate aqueous two-phase droplets [Sauret (2012); Ziemecka (2011b); Song (2012); Vijayakumar (2010); Lee (2012); Ma (2012)], the pressure pulses used here allow for the controlled formation of a single, stationary two-phase droplet with a well-defined time zero. This enables a controlled study of droplet behavior over extended times and can be used to observe dynamic phase transitions.

Example 3

Evaporation-Induced Phase Transitions

By the generation of static single-phase and two-phase droplets, the phase transitions occurring over time were observed using passive evaporation—which causes polymer concentrations to gradually increase until they cross the binodal line and phase separate [Santesson, (2004); Long (2005); Song (2012)].

For example a droplet with a 6 μm diameter has a surface area to volume ratio of 1 μm$^{-1}$. In general, evaporation is enabled by the small amounts of water molecules that are able to diffuse from the microdroplets into the oil, where the maximum possible concentration of water depends on the type of oil used (≈0.3 volume % in soybean oil) [He et al. (2004) Anal. Chem, 76:1222-1227]. The permeability of PDMS allows for the subsequent transport of the water vapor through the walls of the device due to an osmotic pressure difference [Merkel et al. (2000) J. Polym. Sci., Part B: Polym. Phys, 38:415-434].

Figure 3:
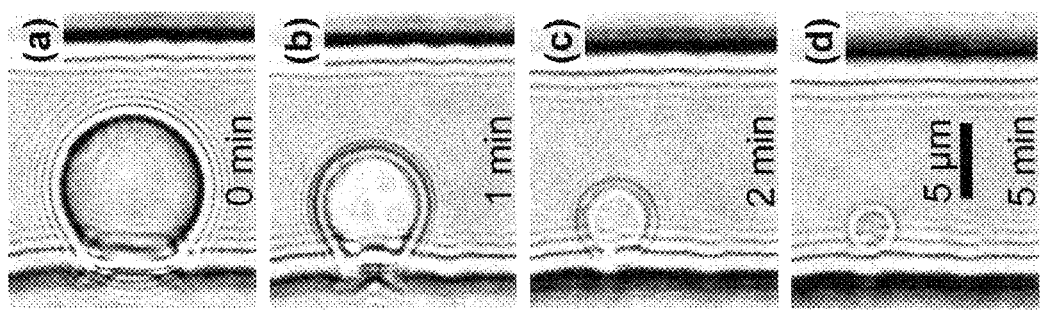
FIG. 3 presents a series of video stills showing the evaporation-induced phase transitions over 5 minutes of (a) a single-phase droplet of 1% PEG and 1% dextran, (b) initial phase nucleation, (c) complete aqueous two-phase separation, and (d) core-shell microbead formation.
Figure 4:
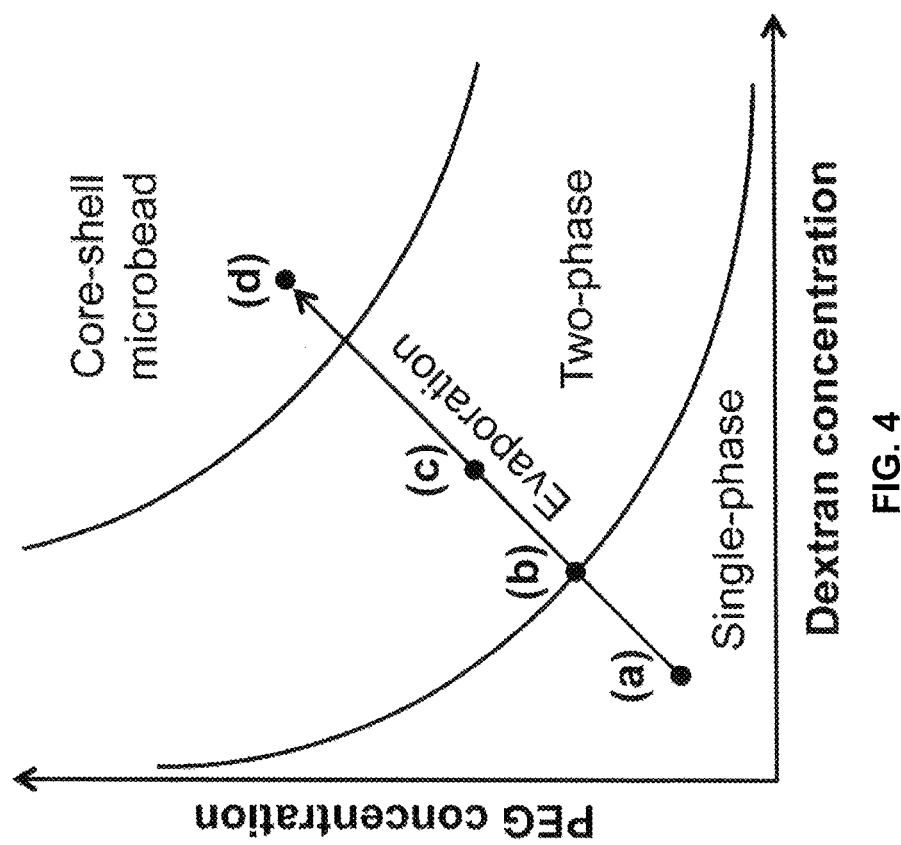
FIG. 4 is a schematic phase diagram, with the straight line depicting the points (a) to (d) of the transitions observed in FIG. 3.

For the evaporation experiments, dry PDMS samples were used in place of the water-soaked samples and allowed an increased droplet shrinkage rate from ~10 μm$^2$ min$^{-1}$ to ~100 μm$^2$ min$^{-1}$ at 25° C. due to the increased osmotic pressure difference. When these microdroplets with large surface area to volume ratios evaporated at this rate, dramatic evaporation-induced phase transitions occurred in a brief time span of only a few minutes (FIG. 3). To ensure that an actuated droplet would initially be well within the single-phase regime, an aqueous solution containing low concentrations of 1% PEG and 1% dextran was used in one of the side-channels. This approach differs from the technique in Example 2 which used a PEG solution in one side-channel and a dextran solution in the opposing side-channel to prevent phase separation from occurring within a side-channel before droplet actuation. A single-phase droplet was generated from the side-channel into the static oil channel (FIG. 3A), and three distinct types of phase transitions were observed over a five minute evaporation time as polymer concentrations increased. First, multiple dextran droplets began to nucleate within the droplet, indicating the beginnings of phase separation (FIG. 3B). Second, the dextran drops continued to grow in size and coalesce together, culminating in complete phase separation (FIG. 3C). Finally, the aqueous two-phase droplet solidified into a core-shell microbead (FIG. 3D), as indicated by a sudden halt in shrinkage to a constant size (see FIGS. 4 and 5 for confirmation of the microbead state). These microbeads were remarkably stable, remaining constant in size and composition even after 48 h had elapsed.

Figure 5:
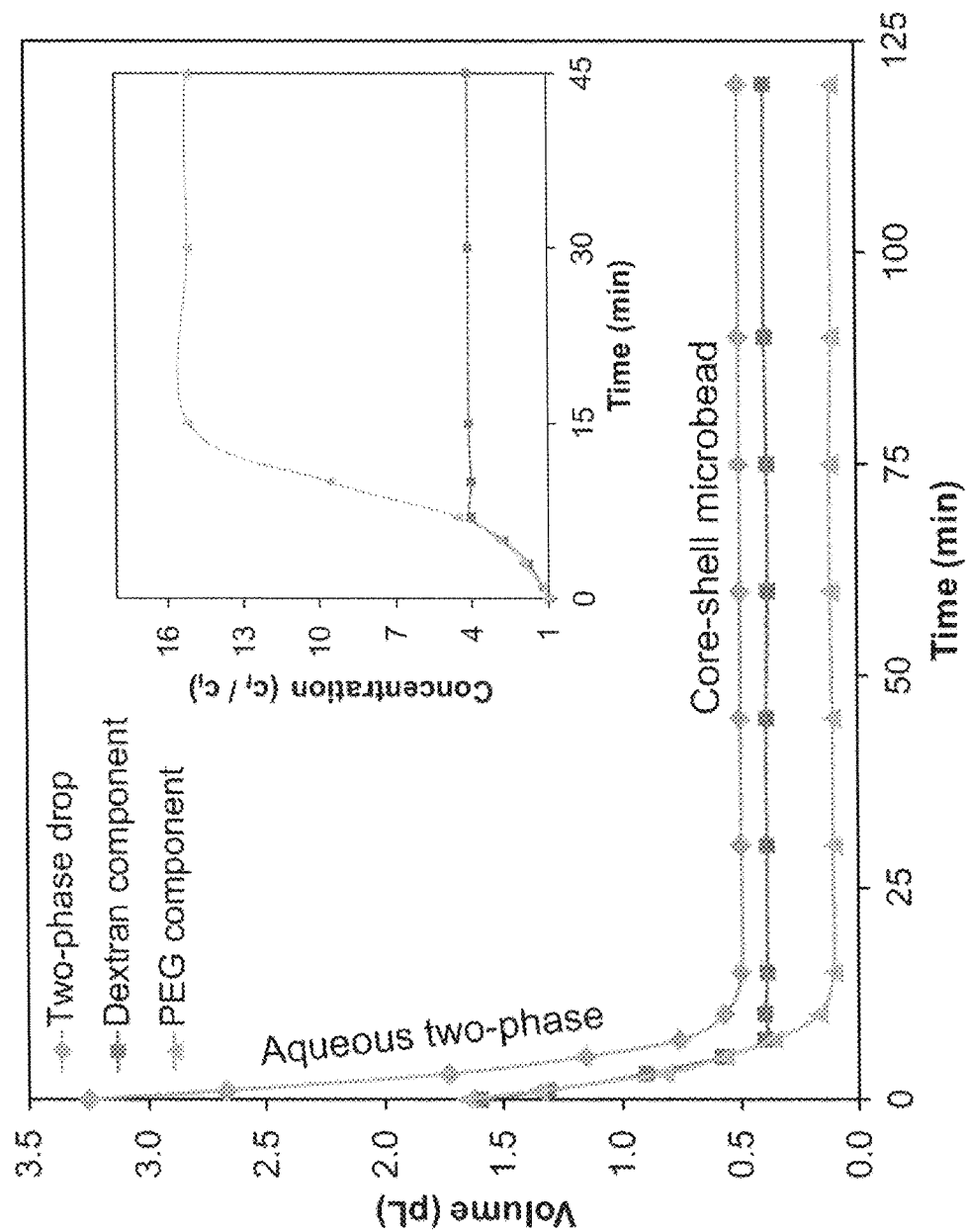
FIG. 5 graphically depicts the change in volume during evaporation of an aqueous two-phase drop into a steady-state core-shell particle for the two-phase droplet (♦), the dextran component (■) and the PEG component (▲). The inset shows the increase in concentration of the inner (dextran-rich, ■) and outer (PEG-rich, ▲) phases during evaporation relative to their initial concentrations ($C_f/C_i$).

In another experiment, increased polymer concentrations of 5% PEG and 5% dextran were used in their respective side-channels to obtain a fused droplet that phase-separated immediately upon coalescence in the oil channel. The volumes of each phase were measured over a span of two hours (FIG. 5). During the first ten minutes of evaporation, the PEG-rich outer phase and the dextran-rich inner phase were observed to evaporate at approximately the same rate, in good agreement with a previous report using a levitated two-phase droplet [Santesson (2004)]. After about ten minutes, however, the evaporation rate dramatically changed to zero for both phases, as evidenced by the near-constant phase volumes over the next two hours, indicating that the aqueous two-phase droplet transitioned to a core-shell particle in the same manner as the previous experiment (FIG. 3D). In this particular case, the core-shell microbead was approximately 10 μm in diameter with a PEG shell thickness of about 1 μm. The ratio of polymer concentration in the solidified core-shell microbead compared to the initial concentration upon actuation was calculated to be approximately 4 for the dextran-rich phase and 14-15 for the PEG-rich phase (FIG. 5, inset). While the initial concentrations used in the side-channels were both 5%, the possibility of partial evaporation in the side-channels before actuation makes it difficult to accurately estimate the final concentrations upon solidification.

Figure 6:
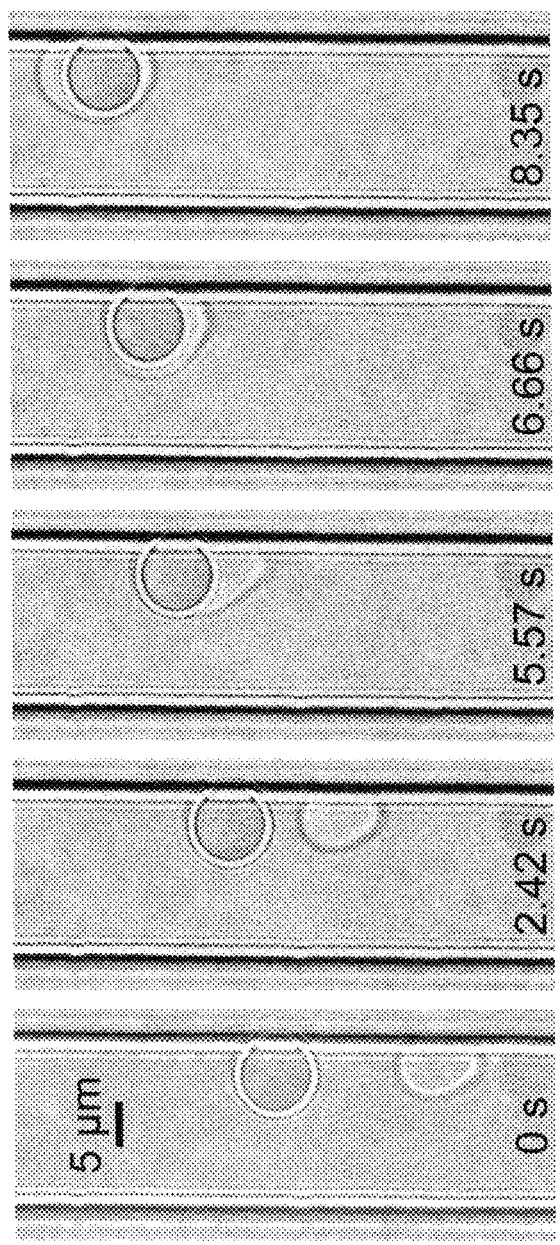
FIG. 6 presents a series of video stills of an aqueous PEG droplet (bottom) and core-shell microbead (top) sliding along the side wall in a flowing oil channel. The solidification of the core-shell microbead is evidenced by a slower sliding velocity, shear-resistant spherical cap, and immiscibility with the aqueous PEG droplet upon fusion.

To confirm that droplets with zero shrinkage rates were solidified microbeads, an aqueous PEG droplet was coalesced with a core-shell microbead (FIG. 6). A microbead was allowed to form in the oil channel and eventually adhered to one of the side-walls. Thereafter, a fresh, purely aqueous PEG droplet was actuated from the side-channel that was on the same wall as the microbead. To cause fusion between the droplet and the microbead, a steady oil flow was generated by applying a constant backing pressure to the central channel. The resulting velocity of the PEG droplet along the side wall was 4.8 µm s$^{-1}$—more than twice as fast as the microbead's velocity of 2.1 µm s$^{-1}$—which allowed the PEG droplet to catch up and fuse with the microbead. The shape of the PEG droplet noticeably sheared during oil flow, in stark contrast to the microbead which remained spherical. Upon coalescence the PEG droplet surrounded the core-shell microbead but the two were unable to mix together, a behavior never observed for purely aqueous coalescence events. Taken together, these observations indicate that transition to a microbead state had occurred. This observation is corroborated by the additional observation that PEG and/or dextran solutions, when left static inside of the 1 µm×1 µm side-channels for a long enough period of time, eventually evaporated into solidified clogs that could not be cleared even with strong backing pressures of several atmospheres.

Example 4

Hydration-Induced Reversible Phase Transitions

A mixture containing both 1% PEG and 1% dextran was placed in one of the side-channels and pure deionized water was placed in the opposing side-channel for hydration experiments. As in Example 3, dry PDMS samples were used to maximize the evaporation rate and accelerate phase transitions to a solidified state.

Figure 7:
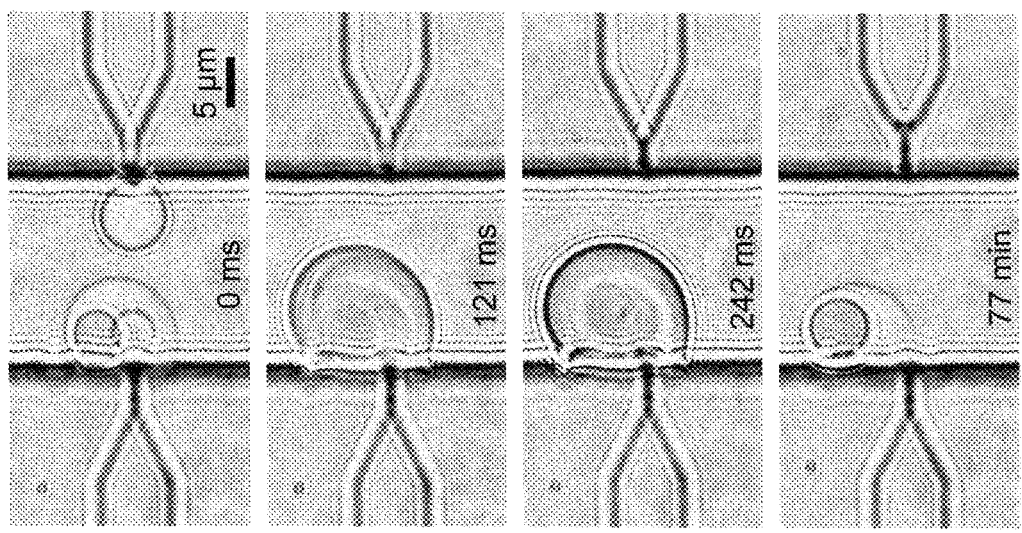
FIG. 7 presents a series of video stills of a microbead with two dextran cores and a PEG shell (left) fusing with a pure water droplet (right) to hydrate back into an aqueous two-phase droplet. The two-phase droplet eventually transitions back into a core-shell microbead after evaporation.

A large droplet was actuated from the polymer side-channel, and allowed to evaporate until phase separation occurred. Due to the large volume of the outer PEG phase, the inner dextran droplet was the first to transition into a particle during continued evaporation, at which point additional solution was injected to obtain two immiscible dextran particles inside of a PEG microbead after complete evaporation. A pure water droplet was then actuated from the other side-channel (FIG. 7, t=0 ms), which upon coalescence (121 ms) immediately transitioned the core-shell particle into an aqueous two-phase droplet (242 ms), as evidenced by the sudden miscibility and coalescence of the inner dextran phases. Finally, the aqueous two-phase droplet was allowed to evaporate back into a microbead (77 min), which now had a single dextran core instead of two due to their fusion during hydration. This dehydration and rehydration cycle was performed four times in succession on the same droplet.

Figure 8:
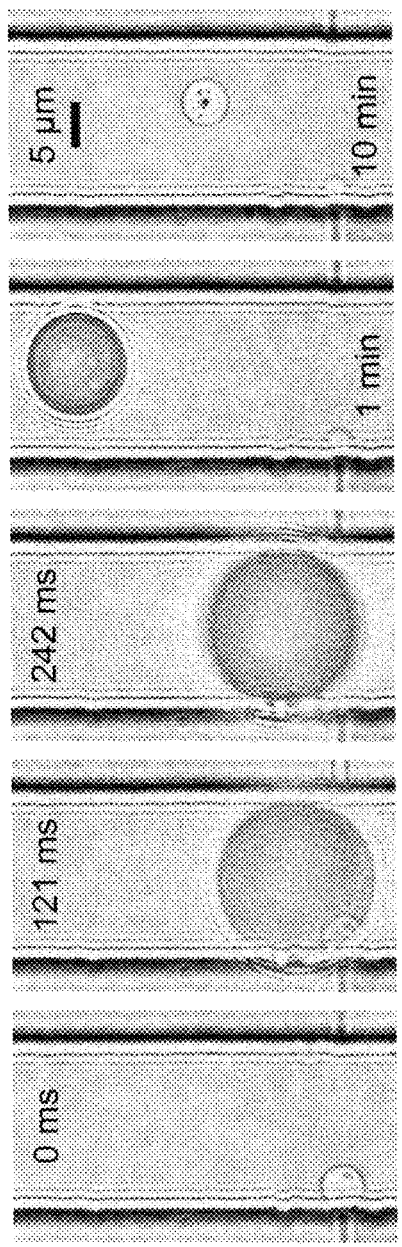
FIG. 8 presents a series of video stills of a microbead being engulfed in a large water droplet and transitioning into a single-phase aqueous droplet. Subsequent evaporation results in partial phase separation and a return to a solidified state.

By decreasing the volume of a microbead and increasing the volume of an actuated water droplet, a complete hydration transition back to a single-phase aqueous droplet was also observed (FIG. 8). As with the previous hydration experiment, the phase transition occurred immediately after coalescence. Approximately one minute after hydration, the dextran phase began to nucleate within the droplet due to evaporation (similar to FIG. 3B), and after ten minutes transitioned back into a microbead. Interestingly, in this particular case the dextran concentration and droplet volume were small enough that solidification into a microbead occurred before the phase separation was fully completed, as indicated by the multiple dextran cores present within the PEG shell.

Example 5

Formation of Femtoliter Microscale Droplet Interface Bilayers (MicroDIBs)

To prepare lipid/oil mixtures for droplet formation, 1,2-dioleoyl-sn-glycero-3-phosphocholine was dissolved in chloroform (DOPC, Avanti Polar Lipids) and dried under a gentle nitrogen flow (1 h, room temperature) followed by vacuum drying (2 h, room temperature). The dried lipids were dissolved in purified soybean oil by shaking overnight (2 mM, 37° C., 250 rpm). For fluorescent imaging, 0.1 mol % of 1,2-dipalmitoyl-sn-glycero-3-phosphoethanolamine-N-(lissamine rhodmine B sulfonyl) (ammonium salt) (DOPC, Avanti Polar Lipids) was added to the DOPC before dissolving in oil.

Figure 9:
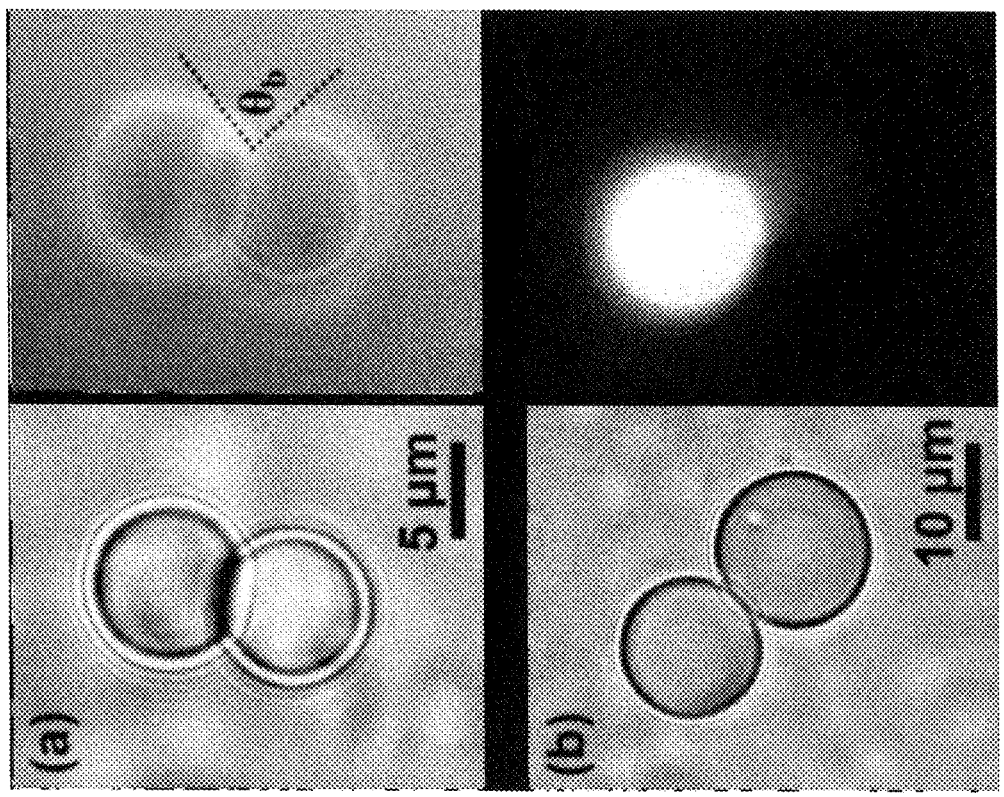
FIG. 9 provides photographs of microscale droplet interface bilayers (microDIBs) formed in an oil microchannel with 2 mM DOPC lipid. (a) Bright-field and fluorescent imaging of microDIBs containing fluorescently tagged lipids; (b) bright-field and fluorescent imaging with fluorescein in one droplet.

Femtoliter droplets were generated and joined together in a lipid-oil microchannel by applying timed pressure pulses to opposing side-channels filled with deionized water as generally described in Example 1 using 2 mM 1,2-dioleoyl-sn-glycero-3-phosphocholine (DOPC) lipid in purified soybean oil and water-soaked PDMS chips [see also, Jung (2010b)] Instead of coalescing, the two water droplets fused to form a microDIB (FIG. 9). The presence of outer lipid monolayers and an inner lipid bilayer was confirmed by fluorescently labeling DOPC with 0.1 mol % 1,2-dipalmitoyl-sn-glycero-3-phosphoethanolamine-N-(lissamine rhodmine B sulfonyl) (ammonium salt) (FIG. 9A, right panel). The lipid bilayer was also identified by selectively adding 250 uM fluorescein into one of the two side-channels containing a Tris buffer solution (pH 8.0), revealing the sharp contrast in fluorescent signal across the bilayer between the droplets (FIG. 9B, right panel). While fluorescein can leak across DIBs without the aid of ion channels [Stanley et al. (2010) J. Chem. Commun. 46:1620-1622], leakage was not observed here due to the dominance of the evaporative time-scale (minutes) over the leakage time-scale (hours). The equilibrium contact angle ($\theta_b$) of 85°±3° for microDIBs formed with pure water droplets (FIG. 9A) was comparable to a previous report [Dixit et al. (2012) Langmuir 28:7442-7451].

The dynamics of evaporating microDIBs were observed and characterized (FIG. 10). A dry PDMS chip was utilized to increase the shrinkage rate by an order of magnitude (~100 µm$^2$/min), resulting in droplet lifetimes of approximately 3 minutes. For the three-phase contact line to remain balanced during evaporation, the droplets needed to maintain the same shape and contact angle ($\theta_b$=85°) as they shrank. During evaporation, the lipids in the bilayer were preserved while the outer monolayer areas preferentially shrink, creating three distinct regimes (FIGS. 10A and B).

In Regime 1 (Shape-Change), as the droplets begin to evaporate, the energetic unfavorability of the bilayer decreasing its area causes the two droplets to morph into hemispheres, so that the system resembles a single spherical droplet. Interestingly, the area of the bilayer interface did not remain constant during droplet shrinkage and shape change, but rather continuously increased from 38 to 54 µm (as estimated by its cross-sectional diameter).

In Regime 2 (Bilayer Buckling), once the droplets finish morphing into the shape of a single sphere, the apparent contact angle remained at $\theta_b$=180° as the system continued to evaporate. The fixed spherical shape of the system resulted in a confined bilayer as evaporation continued. Because lipid bilayers are highly incompressible but exhibit a low bending stiffness [Sackmann (1994) FEBS Lett. 346:3-16; Lis et al. (1982) Biophys. J. 37:667-672], the bilayer buckled into an increasingly curved shape as it became confined. In most trials, the buckling bilayer assumed a sinusoidal shape; however, single-mode buckling was also observed in a minority of droplets. The transition temperature of DOPC is -20° C., well below the experimental temperature of 25° C.; therefore, the lipids in the buckling bilayer are expected to be in the liquid phase. Upon initiation of buckling, the bilayer undulated with amplitudes of ~1 μm. This flickering effect was not observed for the planar bilayers of Regime 1.

In Regime 3 (Fission/Recovery), as the buckling bilayer became increasingly confined, its radius of curvature gradually decreased toward a critical value where fission occurred.

Figure 10A:
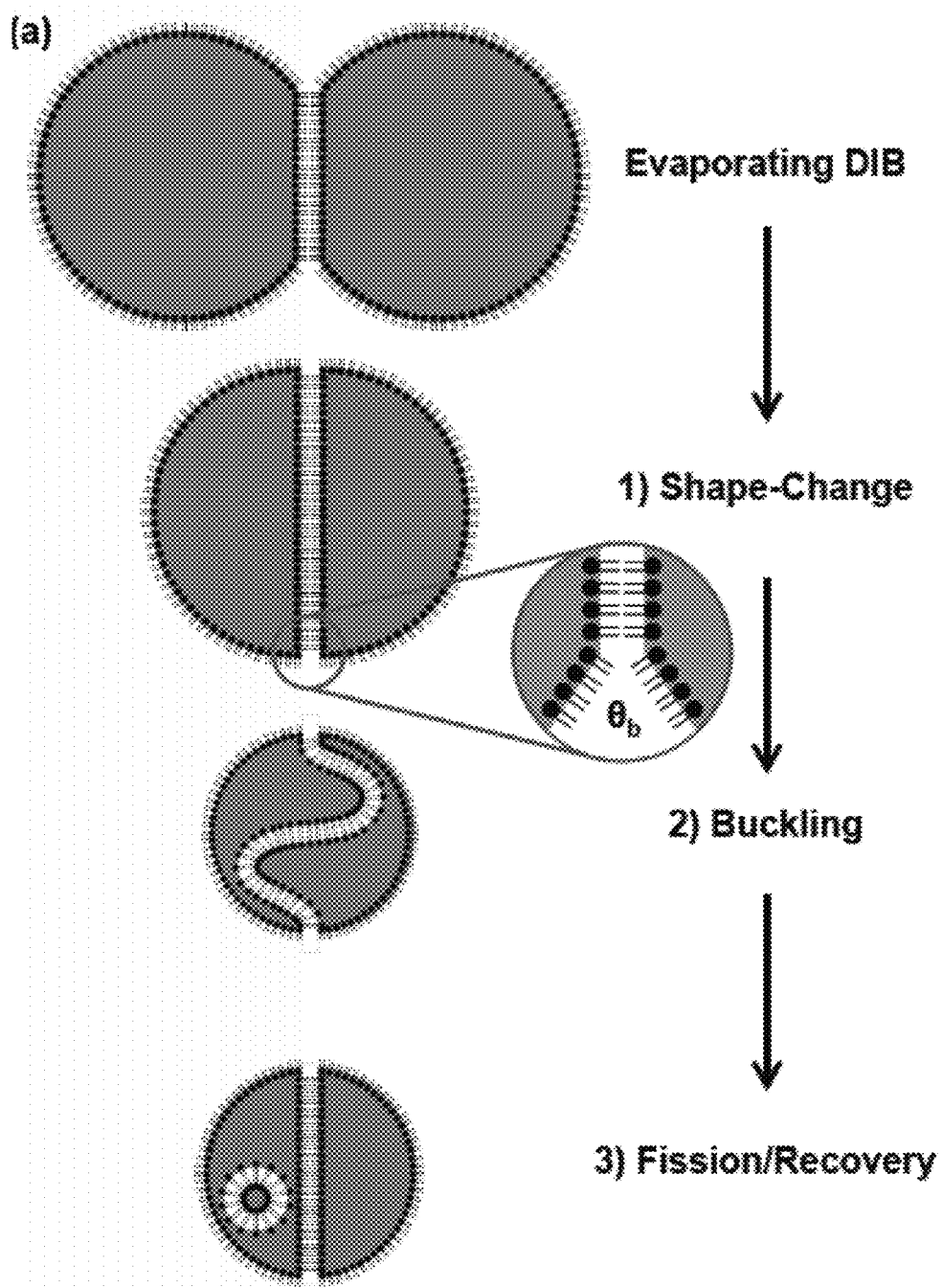
FIGS. 10A and B show (a) schematic and (b) fluorescent images of a microDIB as it undergoes evaporation.
Figure 10B:
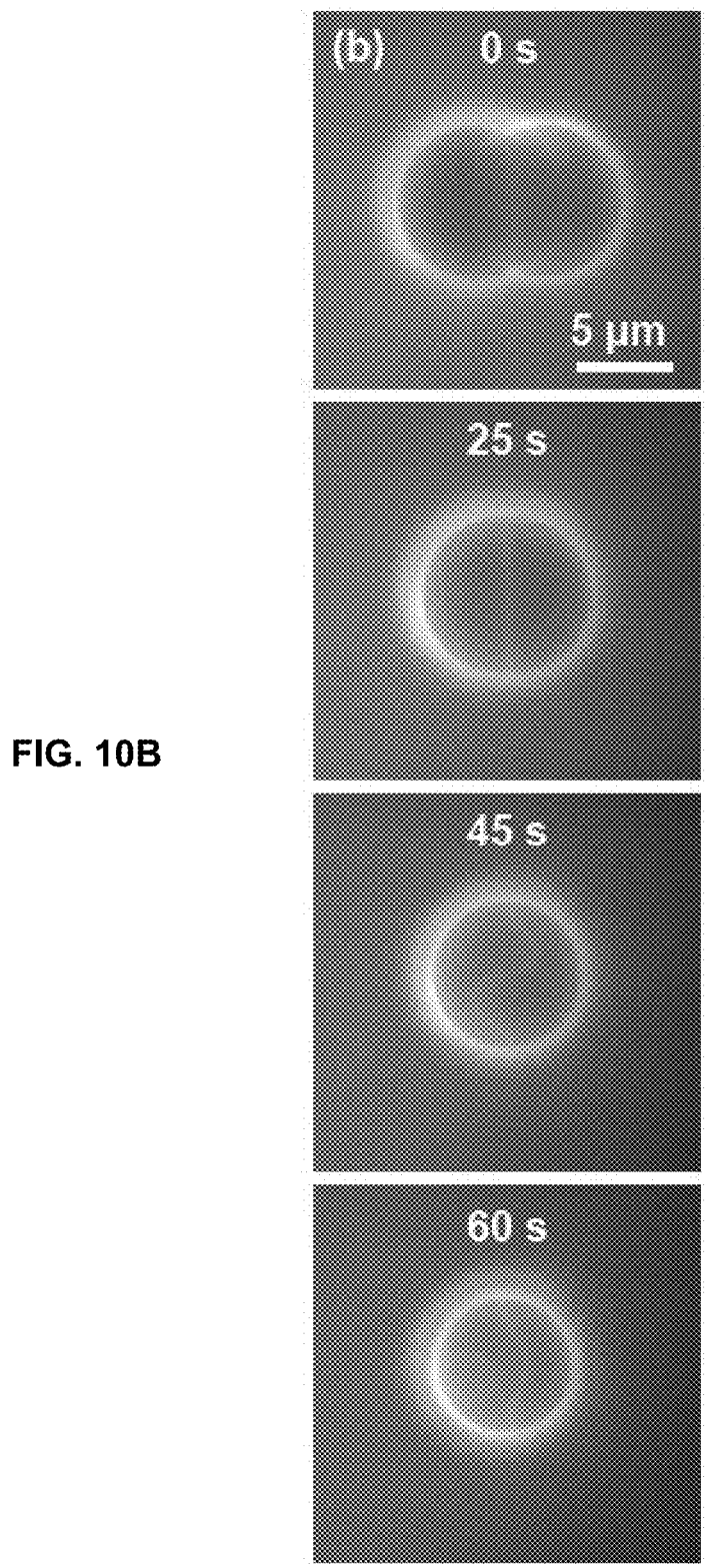
FIG. 10C shows an energy plot versus apparent contact angle as microDIP droplets shrink to a spherical shape ($\theta_b^*=180°$) to minimize the surface energy of the monolayer interfaces.
FIG. 10D shows a plot of bilayer length over time and the bending moment over time as the bilayer is continuously fed by lipids from the shrinking monolayers, resulting in buckling and eventually fission at a bending moment corresponding to a critical shear stress. Fission serves to rectify the bilayer's shape and stress.
Figure 10C:
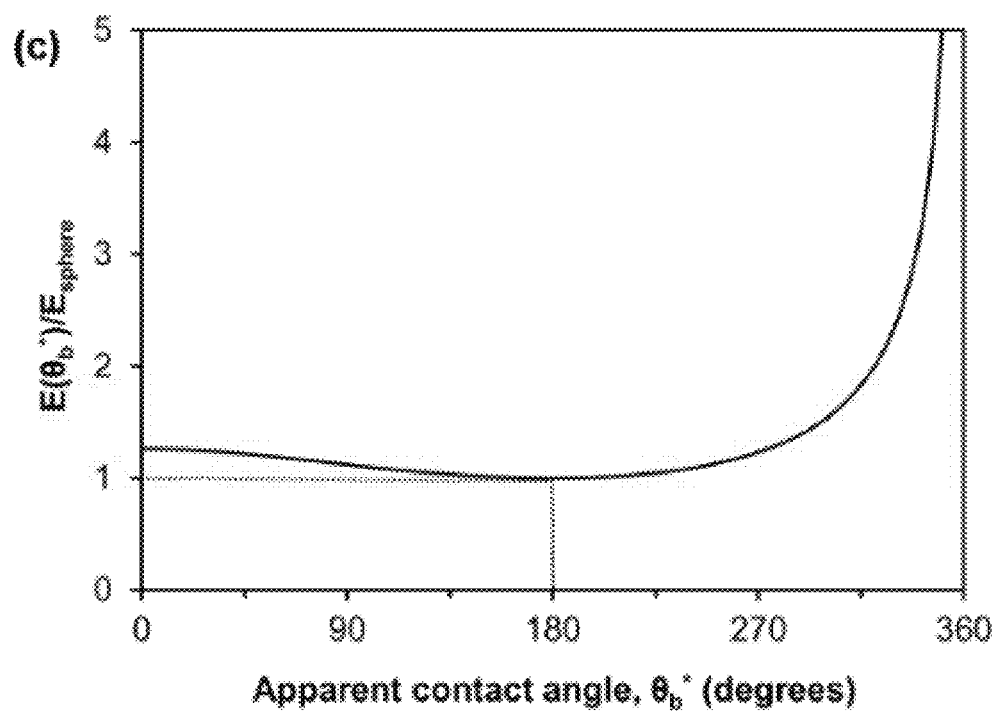

For the lipids in the evaporating microDIBs to conserve their mass, the area lost in the monolayers should be half the area gained by the bilayer (as in FIG. 10A). The total area of the buckling bilayer at its critical curvature was estimated by adding together the areas of the spherical vesicle and (nearly) planar bilayer immediately after fission occurred. The surface area lost by the monolayer interfaces from time zero to fission ($\approx 85$ $\mu m^2$ in FIG. 10B) was slightly larger than double the area gained by the bilayer ($\approx 55$ $\mu m^2$). The 30 $\mu m^2$ of unaccounted area lost by the monolayers was ~10% of the total lipid area, and is either due to a slight increase in packing density or limitations in estimating the 3D surface areas from a 2D cross-section.

Figure 10D:
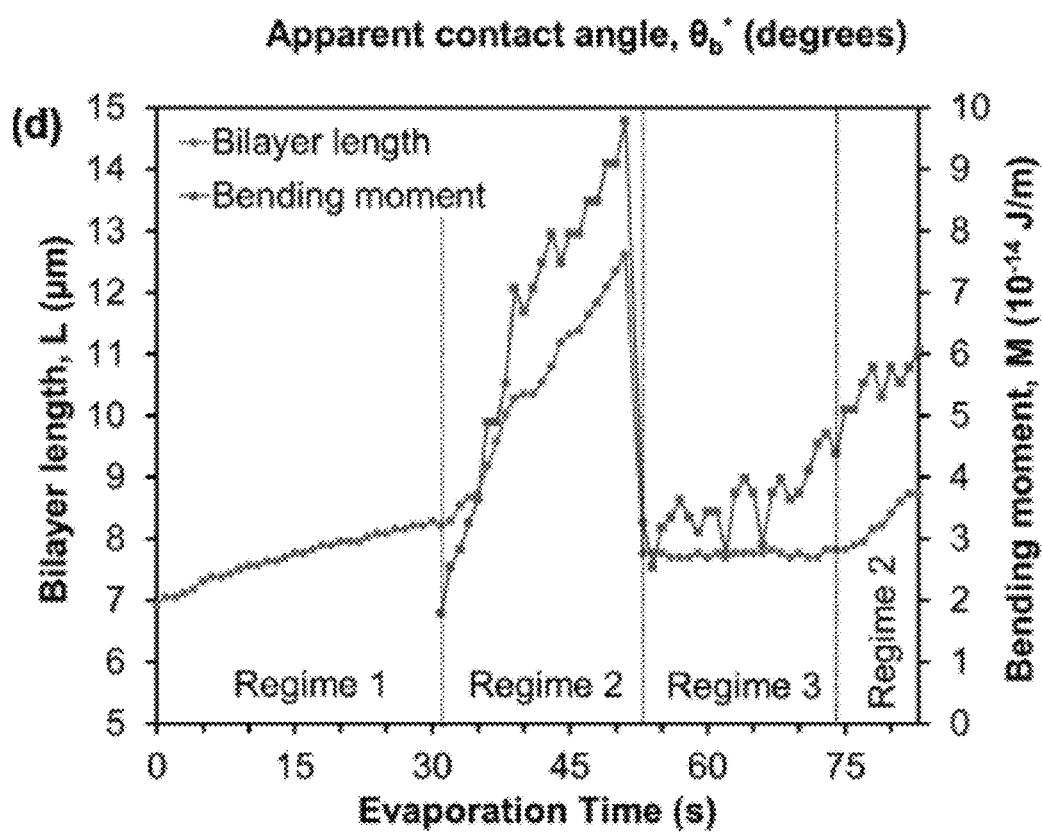

The rupture of the buckling bilayer served to rectify its shape and stress (FIG. 10D). Rupture resulted in the fission of a small lipid vesicle (D≈2 μm) from the bilayer into the aqueous droplet, reducing the bilayer's area and allowing it to approximate its original planar configuration. As the droplet continued to shrink, the bilayer buckled once more, revealing that the system will continue to cycle between Regimes 2 and 3 until the droplets have lost all water content. Vesicles were observed to eventually fuse to the interior of a monolayer interface, drawing lipids from it in a manner similar to the original bilayer. It was also observed that when one droplet was appreciably larger than its partner, the bilayer preferentially buckled and fissioned toward the larger droplet due to the asymmetric shape-change.

We claim:

1. A method for forming an aqueous two-phase microdroplet, the method comprising:
   providing a microfluidic device comprising a central microchannel having a communication junction with a first side microchannel, wherein said first side microchannel contains an aqueous solution comprising a single-phase mixture of first and second solutes capable of phase separation with each other but present at concentrations sufficiently below the binodal curve of the single-phase mixture in order for the first and second solutes to remain in a single phase in said aqueous solution at the time of microdroplet formation, and said central microchannel contains an aqueous-immiscible phase, and wherein the height and width of said first side microchannel at said communication junction are sufficiently smaller than the height and width of said central microchannel;
   generating a single-phase aqueous microdroplet, composed of said aqueous solution, into said central microchannel by applying a pressure pulse through said first side microchannel of the microfluidic device, wherein the pressure pulse creates an interfacial tension induced force sufficient for said first aqueous microdroplet to have a diameter of from about 0.2 μm to about 100 μm, and
   allowing passive water evaporation from said single-phase aqueous microdroplet to occur until a two-phase aqueous microdroplet containing first and second aqueous phases is formed in said central microchannel.

2. The method of claim 1, comprising:
   providing a microfluidic device comprising a central microchannel having a communication junction with a first side microchannel and, approximately opposing said first side microchannel, having a communication junction with a second side microchannel, said central microchannel containing an aqueous-immiscible phase, said first side microchannel containing a first aqueous solution and said second side microchannel containing a second aqueous solution, wherein said first and second aqueous phases solutions contain first and second solutes, respectively, capable of phase separation with each other but present in said first and second aqueous solutions at concentrations sufficiently below the binodal curve of a mixture of said first and second aqueous solutions in order for the two solutes to be in a single phase when combined into a microdroplet, and wherein the height and width of said first and second side microchannels at said communication junctions are sufficiently smaller than the height and width of said central microchannel;
   generating a first aqueous microdroplet composed of the first aqueous solution, into said central microchannel by applying a pressure pulse through said first side microchannel of the microfluidic device, wherein the pressure pulse creates an interfacial tension induced force sufficient for said first aqueous microdroplet to have a diameter of from about 0.2 μm to about 100 μm;
   generating a second aqueous microdroplet composed of the second aqueous solution, into said central microchannel by applying a pressure pulse through said second side microchannel in said microfluidic device, wherein the pressure pulse creates an interfacial tension induced force sufficient for said first aqueous microdroplet to have a diameter of from about 0.2 μm to about 100 μm;
   allowing said first and second aqueous microdroplets to coalesce in said central microchannel to form a single-phase aqueous microdroplet that contains a mixture of said first and second solutes in a single phase; and
   allowing passive water evaporation from said single-phase aqueous microdroplet to occur until a two-phase microdroplet containing first and second aqueous phases is formed in said central microchannel.

3. The method of claim 1, wherein said aqueous-immiscible phase is an oil or mixture of oils.

4. The method of claim 3, wherein said oil is soybean oil.

5. The method of claim 1, wherein said pressure pulse creates an interfacial tension induced force sufficient to form a microdroplet having a diameter of from about 1 μm to about 20 μm.

6. The method of claim 5, wherein said pressure pulse creates an interfacial tension induced force sufficient to form a microdroplet having a diameter of from about 5 μm to about 15 μm.

7. The method of claim 1, wherein the height and width of the first side microchannel independently ranges from about 0.2 μm to about 3 μm, and the height and width of the central microchannel independently ranges from about 10 μm to about 40 μm.

8. The method of claim 1, wherein the height and width of said first side microchannel independently ranges from approximately 0.1 μm to about 5 μm.

9. The method of claim 1, wherein the height and width of said central microchannel independently ranges from about 1 μm to about to about 300 μm.

10. The method of claim 1, wherein one or both of said first or second aqueous phases comprise one or more biomolecules capable of partitioning between said first and second aqueous phases.

11. The method of claim 1, further comprising one or more biomolecules that do not partition between said first and second aqueous phases, and one or more biomolecules that partition between said first and second aqueous phases.

12. The method of claim 1, further comprising one or more biomolecules that do not partition between said first and second aqueous phases.

13. A method of making a microparticle preparation, the method comprising:
(a) applying multiple pressure pulses to generate aqueous two-phase microdroplets according to the method of claim 1;
(b) applying a backing pressure to the central microchannel to move the aqueous two-phase microdroplets into a collection reservoir while allowing passive water evaporation to occur until each aqueous two-phase microdroplet remains at a constant size to form core-shell microbeads,
(c) recovering said core-shell microbeads from said collection reservoir to thereby produce a microparticle preparation.

14. The method of claim 13 wherein one or more of said aqueous solutions used in forming said aqueous two-phase microdroplets comprise a drug.

15. A drug delivery formulation which comprises a microparticle preparation prepared by the method of claim 13 and a pharmaceutically-acceptable carrier.

16. The method of claim 1, further comprising reversible conversion of said two-phase aqueous microdroplet into a single-phase aqueous microdroplet by fusing said two-phase aqueous microdroplet with a microdroplet of water.

17. The method of claim 1, wherein said first and second solutes are first and second polymers, respectively.

18. The method of claim 17, wherein said first polymer is PEG and said second polymer is dextran.

* * * * *